US010111947B2

(12) United States Patent
Sene et al.

(10) Patent No.: US 10,111,947 B2
(45) Date of Patent: Oct. 30, 2018

(54) VIRUS-CONTAINING FORMULATION AND USE THEREOF

(71) Applicant: Transgene S.A., Illkirch Graffenstaden (FR)

(72) Inventors: Claude Sene, Strasbourg (FR); Mélina Chasle, Strasbourg (FR)

(73) Assignee: Transgene S.A., Illkirch Grafffenstaden (FR)

( * ) Notice: Subject to any disclaimer, the term of this patent is extended or adjusted under 35 U.S.C. 154(b) by 0 days.

(21) Appl. No.: 14/433,142

(22) PCT Filed: Oct. 2, 2013

(86) PCT No.: PCT/EP2013/070590
§ 371 (c)(1),
(2) Date: Apr. 2, 2015

(87) PCT Pub. No.: WO2014/053571
PCT Pub. Date: Apr. 10, 2014

(65) Prior Publication Data
US 2015/0250869 A1   Sep. 10, 2015

(30) Foreign Application Priority Data
Oct. 2, 2012   (EP) .................................... 12306198

(51) Int. Cl.
*C12N 7/00* (2006.01)
*A61K 39/285* (2006.01)
(Continued)

(52) U.S. Cl.
CPC .............. *A61K 39/285* (2013.01); *A61K 9/19* (2013.01); *A61K 47/183* (2013.01); *A61K 47/26* (2013.01);
(Continued)

(58) Field of Classification Search
None
See application file for complete search history.

(56) References Cited

U.S. PATENT DOCUMENTS 3,915,794 A    10/1975  Zygraich et al.
4,338,335 A *   7/1982  McAleer ................ A61K 39/12
                                                 424/212.1
(Continued)

FOREIGN PATENT DOCUMENTS

CN          1640496 A      7/2005
EP          0 872 249      10/1998
(Continued)

OTHER PUBLICATIONS

Maeda et al., "Effects of the naturally-occurring disaccharides, palatinose and sucrose, on incretin secretion in healthy non-obese subjects," Journal of Diabetes Investigation, vol. 4, Issue 3: 281-286 (2013).*
(Continued)

Primary Examiner — Janet L Andres
Assistant Examiner — M Franco G Salvoza
(74) Attorney, Agent, or Firm — Buchanan Ingersoll & Rooney PC

(57) ABSTRACT

The present invention relates to formulation comprising (i) at least one virus-based material, (ii) at least one polymer selected in the group of polyvinylpyrrolidone and derivatives thereof, (iii) at least one sugar, (iv) at least two different amino acids, (v) at least two pharmaceutical acceptable salts, wherein at least one of said salts is a phosphate salt and, optionally (vi) a pharmaceutical acceptable buffer. Such a formulation is particularly suitable for freeze-drying. The present invention also relates to the corresponding dry product, as well as its preparation process. The present invention also relates to a reconstituted material comprising said dry product, which can be administered to a patient in
(Continued)

need thereof. Such formulation and reconstituted material are useful as vaccines, preferably for the treatment and/or the prevention of cancers, infectious diseases and/or autoimmune disorders.

15 Claims, 2 Drawing Sheets

(51) Int. Cl.
*A61K 47/18* (2017.01)
*A61K 47/32* (2006.01)
*A61K 9/19* (2006.01)
*A61K 47/26* (2006.01)
*A61K 47/02* (2006.01)

(52) U.S. Cl.
CPC ............... *A61K 47/32* (2013.01); *C12N 7/00* (2013.01); *A61K 47/02* (2013.01); *C12N 2710/24134* (2013.01); *Y02A 50/463* (2018.01); *Y02A 50/481* (2018.01)

(56) References Cited

U.S. PATENT DOCUMENTS

| | | | |
|---|---|---|---|
| 4,500,512 A | | 2/1985 | Barme |
| 4,777,026 A | * | 10/1988 | Griffith ............... C01B 25/28 423/157.2 |
| 5,618,539 A | * | 4/1997 | Dorval ............... A61K 39/13 424/217.1 |
| 6,210,683 B1 | * | 4/2001 | Burke ............... A61K 39/165 424/212.1 |
| 2005/0019349 A1 | | 1/2005 | Howley et al. |
| 2006/0110331 A1 | * | 5/2006 | Dang ............... A61K 9/0043 424/45 |
| 2006/0204511 A1 | * | 9/2006 | Bouwstra ............... A61K 47/34 424/185.1 |
| 2007/0048327 A1 | * | 3/2007 | Bartlett ............... A61K 31/4035 424/184.1 |
| 2011/0081380 A1 | * | 4/2011 | Francon ............... A61K 39/12 424/224.1 |
| 2011/0243988 A1 | * | 10/2011 | Ohtake ............... A61K 39/0275 424/212.1 |

FOREIGN PATENT DOCUMENTS

| | | |
|---|---|---|
| EP | 1 418 942 | 5/2004 |
| WO | WO 89/06542 | 7/1989 |
| WO | WO 92/07000 | 4/1992 |
| WO | WO 92/15672 | 9/1992 |
| WO | WO 95/09241 | 4/1995 |
| WO | WO 95/10601 | 4/1995 |
| WO | WO 97/23238 | 7/1997 |
| WO | WO 03/053463 | 7/2003 |
| WO | 2005/066333 A1 | 7/2005 |
| WO | WO 2005/066333 | 7/2005 |
| WO | WO 2006/094974 | 9/2006 |
| WO | WO 2007/056847 | 5/2007 |
| WO | WO 2008/114021 | 9/2008 |
| WO | WO 2009/065546 | 5/2009 |
| WO | WO 2009/065547 | 5/2009 |
| WO | WO 2010/130753 | 11/2010 |
| WO | WO 2011/129120 | 10/2011 |

OTHER PUBLICATIONS

European Food Safety Authority, "Opinion of the Scientific Panel on Dietetic Products, Nutrition and Allergies on a request from the Commission related to the Tolerable Upper Intake Level of Chloride," The EFSA Journal 210: 1-9 (2005).*
Eldred et al., "Vaccine components and constituents: responding to consumer concerns," Med J Aust 184(4): 170-175 (2006).*
Adams, *The Principles of Freeze-Drying*, 368 Methods in Molecular Biology 15-38 (2007).
Day et al., *Cryopreservation and Freeze-Drying Protocols*, 38 Methods in Molecular Biology 254 (377 Book Review/FEBS Letters 280-284) (1995) (abstract only).
Goebel et al., Appendix to "*The Complete DNA Sequence of Vaccinia Virus*," 179 Virology 517-563 (1990).
Goebel et al., *The Complete DNA Sequence of Vaccinia Virus*, 179 Virology 247-266 (1990).
Croyle et al., *Factors That Influence Stability of Recombinant Adenoviral Preparations for Human Gene Therapy*, 3(3) Pharmaceutical Development and Technology 373-383 (1998).
Jennings, *Product Properties*, Lyophilization—Introduction and Basic Principles 415-418 (1999).
Paoletti et al., *Highly Attenuated Poxvirus Vectors: NYVAC, ALVAC and TROVAC*, 84 Dev Biol Stand. Basel, Karger 159-163 (1995).
Sutter et al., *A recombinant vector derived from the host range-restricted and highly attenuated MVA strain of vaccinia virus stimulates protective immunity in mice to influenza virus*, 12(11) Vaccine 1032-1040 (1994).
Tartaglia et al., *NYVAC: A Highly Attenuated Strain of Vaccinia Virus*, 188 Virology 217-232 (1992).
International Search Report issued in corresponding PCT Application PCT/EP2013/070590 dated Dec. 17, 2013.
International Search Report issued dated Dec. 17, 2013, in corresponding application PCT/EP2013/070590.
Burke et al., Formulation, Stability, and Delivery of Live Attenuated Vaccines for Human Use, 16(1) Therapeutic Drug Carrier Systems, 1-83 (1999).
Rexroad et al., Lyophilization and the Thermostability of Vaccines, 1(2) Cell Preservation Technology 91-104 (2002).
Orvell, Measles Virus, Encyclopedia of Virology, 838-841 (1994).
Wittek, Vaccinia Virus, Encyclopedia of Virology, 1507-1509 (1994).

* cited by examiner

VIRUS-CONTAINING FORMULATION AND USE THEREOF

CROSS-REFERENCE TO RELATED APPLICATIONS

This application is a U.S. National Stage Application pursuant to 35 U.S.C. § 371 of International Patent Application PCT/EP2013/070590, filed on Oct. 2, 2013, and published as WO 2014/053571 on Apr. 10, 2014, which claims priority to European Patent Application 12306198.8, filed on Oct. 2, 2012, all of which are incorporated herein by reference in their entireties for all purposes.

TECHNICAL FIELD

The present invention pertains to the field of formulation of biologically active materials such as virus-based materials (e.g. viruses, viral particles, viral vaccine, ... ) or, and more precisely to formulation suitable for their storage. It also relates to the preparation of such formulation. More precisely, the present invention concerns a formulation comprising (i) a virus-based material (ii) at least one polymer selected in the group of polyvinylpyrrolidone and derivatives thereof, (iii) at least one sugar, (iv) at least two different amino acids, (v) at least two pharmaceutically acceptable salts wherein at least one of said salts is a phosphate salt and, optionally (vi) a pharmaceutically acceptable buffer. More particularly, the formulation of the Invention is suitable for drying processes, more particularly freeze-drying processes. The Invention further concerns the obtained dried product, and more particularly the obtained freeze-dried product. The formulations and dried products according to the present invention are useful as vaccine for preventing and/or treating disorders such as cancer, autoimmune diseases and infectious diseases.

BACKGROUND OF THE INVENTION

Storage and shipping of biologically active materials used, for example, in pharmaceutical industry are problematic since these materials are prone to degradation, especially thermal degradation. This is particularly true in case of biologically active materials such as vaccines which can be distributed worldwide and may thus be submitted to different temperatures depending on the countries of distribution or to temperature variation during transport. This further limits distribution of the biological materials to developing nations with limited infrastructure.

Therapeutic activity of virus-based materials, including viruses, viral particles, viral vaccine, requires that their structural integrity is maintained during storage and/or shipping in order to be infectious and/or biologically active.

This structural integrity of a virus-based material is often compromised during the formulation process, thus precluding its therapeutic use. Said therapeutic activity further requires that the viral titer loss, and particularly the infectious titer loss, is limited.

Developing new methods or formulations in order to stabilize biologically active materials for industrial applications such as vaccines, to improve storage and shipping abilities of these biological materials is thus a continuous goal of the pharmaceutical industry.

One of the proposed solutions has been to maintain the biologically active materials within specific temperature ranges, more particularly at low temperatures, i.e. below 0° C., more particularly until −30° C. and even more preferably until −80° C. This ultra-low temperature storage not only is very expensive, but creates significant inconvenience for storage, transportation and clinic use. It was thus necessary to develop formulations that can be stored at refrigerated condition.

According to one alternative, it has thus been proposed to formulate the biologically active materials with additives of animal or human origin such as albumin, peptone, gelatine or haemaccel. However, the use of such components is limited by safety issues such as risks of allergic reactions or risks of contamination with or transmission of infectious agent (e.g. BSE (Bovine Spongiform Encephalopathy). Additionally, this solution is generally expensive and thus is not compatible with industrial development.

Moreover it is assumed that virus-based material will not maintain its infectivity when stored at refrigerated condition in a liquid form for extended period of time. As a result, there are no reported studies on formulating and storing virus at refrigerated condition in a liquid form. Thus, there remains a need for long-term storage stable formulations of viral preparations.

Another alternative was to preserve the biologically active materials, especially virus-based materials, in a dried form. Among the available techniques of drying biomaterial, freeze-drying (also called lyophilization) represents a key step for manufacturing bio-pharmaceuticals such as vaccines. Freeze-drying leads to dried biological products which are stable at about 4° C. to 8° C. and in some cases until about 25° C. Lyophilization has been used widely to improve the stability of various viral vaccine and recombinant protein products.

Freeze-drying process involves successive steps of freezing solutions or suspensions of biomaterials, followed by primary and secondary drying steps (for a review, see Adams, 2007, Methods Mol. Biol. 368, 15-38). Basically, this technique is based on sublimation of water at subzero temperature under vacuum without the solution melting. However, the rate of water vapor diffusion from the frozen biomaterial is very low and therefore the process is time-consuming. Additionally, both the freezing and drying stages introduce stresses (e.g. concentration of salts, precipitation/crystallization, shear stress, pH extremes, residual moisture remaining through the freeze-drying process, ... ) that can force the biological material to undergo significant chemical and physical changes and be very damaging to some biological materials such as virus-based materials. It is thus necessary to have adapted formulations allowing preserving the biologically active material during the drying process, and advantageously further during storage/shipping steps.

The prior art provides examples of formulations used for freeze-drying biological materials, more precisely virus-based materials.

In order to limit infectious titer loss of poliovirus preparation, WO89/06542 has proposed to dry the virus stock solution at 37° C. in the presence of a stabilizing solution made up of 10% trehalose as sole protective agent. However, the drop in infectious titer remains large and greater than that observed for the non-dried vaccine.

EP 0 872 249 describes recombinant virus vector preparation comprising a combination of glutamic acid or its sodium salt and glucose.

WO 95/10601 discloses an aqueous recombinant virus solution comprising a saccharide, a high molecular weight structural additive, an amino acid, a buffer and water.

WO 03/053463 discloses vaccinia virus formulations comprising sucrose, dextran, glutamic acid and a buffer which is free of phosphate.

WO 2005/066333 describes a viral composition comprising urea, a sugar, a salt, a buffer, a dispersing agent and a mixture of essential and non-essential amino acids.

WO 2007/056847 discloses a virus-containing formulation comprising sucrose, sorbitol, a polyvinyl pyrrolidone, urea, a TRIS buffer, monosodium glutamate and another amino acid such as arginine, alanine, serine or glycine.

WO2008/114021 and WO2011/121306 describe viral compositions comprising polyethyleneimine compounds, optionally in combination with one or more sugar(s).

Nevertheless, there remains a need for new formulations allowing stabilization of biological materials, and particularly virus-based materials, allowing industrial applications, storage without affecting biological activity of the product, and more particularly to avoid virus titer loss.

The present Invention provides formulation containing virus-based materials, more particularly aqueous formulation, suitable for freeze-drying. According to preferred embodiment, the formulation of the Invention are stable over long-term stability tests as defined hereinafter and more particularly during storage at temperatures above 0° C., particularly between about 4° C. and about 30° C., preferably between about 4° C. and about 25° C., more preferably between about 2° C. and about 8° C., and even more preferably between about 4° C. and about 5° C. (e.g. refrigerated temperature).

DISCLOSURE OF THE INVENTION

Formulation

According to a first embodiment, the present invention concerns a formulation comprising (i) at least one virus-based material, (ii) at least one polymer selected in the group of polyvinylpyrrolidone and derivatives thereof, (iii) at least one sugar, (iv) at least two different amino acids, (v) at least two pharmaceutical acceptable salts, wherein at least one of said salts is a phosphate salt and, optionally (vi) a pharmaceutical acceptable buffer.

Unless otherwise stated, the following terms as used throughout the entire application, have the following meaning.

"And/or" herein includes the meaning of "and", "or" and "all or any other combination of the elements connected by said term".

"Comprising" and "comprise(s)" are intended to mean that the materials, products, formulations, compositions and methods include the referenced components or steps, but not excluding others. "Consisting essentially of" or "consist(s) essentially of", when used to define products, compositions and methods, shall mean excluding other components or steps of any essential significance. Thus, for example, a composition consisting essentially of the recited components would not exclude trace contaminants and pharmaceutically acceptable carriers. "Consisting of" or "consist(s) of" shall mean excluding more than trace elements of other components or steps.

"About" or "approximately", as used herein, means within 10%, and more preferably within 5% of a given value or range. According to a special embodiment of this definition, "about x" also includes x.

According to preferred embodiment, the formulation of the present invention is an aqueous formulation. Such a formulation is suitable for storage at refrigerated temperature or for storage at non refrigerated temperature (e.g. ambient temperature) especially upon freeze-drying.

According to the present Invention, "virus-based material or product" means viruses, viral particles, viral vectors and viral vaccine. Those terms are synonyms and are interchangeable. This term includes wild type viruses, killed, live attenuated, inactivated and recombinant viruses. It further includes virus-based products such as viral vectors, viral particles such as virus-like particles (VLPs) or nucleocapsids.

According to the present invention, "viruses" relates preferably to those used in vaccines and more preferably to DNA viruses, such as Adenoviridae, Herpesviridae and Poxviridae.

According to more preferred embodiment, "viruses" intends to designate a poxviral vector. Poxviruses according to the present invention more preferably refer to Chordopoxviruses (vertebrate poxviruses). Chordopoxviruses include but are not limited to Orthopoxviruses, Parapoxviruses, Avipoxviruses, Capripoxviruses, Lepripoxviruses, Suipoxviruses, Molluscipoxviruses or Yatapoxviruses. Preferred Chordopoxviruses according to the invention are Orthopoxviruses. According to another preferred embodiment it is selected in the group consisting of vaccinia virus, suitable vaccinia viruses include without limitation the Copenhagen strain (Goebel et al., 1990, Virol. 179, 247-266 and 517-563; Johnson et al., 1993, Virol. 196, 381-401), the Wyeth strain, Elstree, Western Reserve (WR), IHDJ, and the highly attenuated virus derived thereof including MVA, NYVAC (see WO 92/15672—Tartaglia et al., 1992, Virology, 188, 217-232). The vector may also be obtained from any other member of the poxviridae, in particular fowlpox (e.g. TROVAC, see Paoletti et al, 1995, Dev Biol Stand., 84, 159-163); canarypox (e.g. ALVAC, WO 95/27780, Paoletti et al, 1995, Dev Biol Stand., 84, 159-163); pigeonpox; swinepox and the like.

According to one embodiment, the viral vector is a replication competent vector capable of infecting mammalian cells, particularly dividing cells (i.e. oncolytic vectors), and more specifically is replication competent poxviral vector selected in the group consisting of a Vaccinia virus strains Copenhagen or WR (see for example WO2009/065547, WO 2009/065546 or WO9531105).

According to another embodiment, the viral vector is an attenuated poxvirus, characterized by the loss of its capability to reproductively replicate in human cell lines.

According to a preferred embodiment, the virus-based material of the present invention is a virus or viral particle selected from the group consisting of Vaccinia Virus (VV) and modified Vaccinia Virus Ankara (MVA).

Preferred W may be W as described in patent applications WO2009/065546, WO2009/065547 or WO95/31105 describing namely W armed with an immune-stimulating cytokine which is GM-CSF or with a suicide gene.

The invention is preferably carried out with modified vaccinia virus Ankara (MVA) (Sutter et al., 1994, Vaccine, 12, 1032-40). A typical MVA strain is MVA 575 that has been deposited at the European Collection of Animal Cell Cultures under the deposition number ECACC V00120707. Other examples of MVA strains usable according to the Invention are MVA strain deposited at CNCM under number No I-721, MVA-BN deposited at ECACC under number V00083008. MVA II/85, MVA-572 deposited at ECACC under the deposition number V94012707, or a derivative of any such virus.

As previously defined, a virus according to the present invention may be a wild type, attenuated or recombinant virus, more preferably a recombinant poxvirus.

The term "recombinant" virus refers to a virus, more particularly a poxvirus, comprising an exogenous sequence inserted in its genome. As used herein, an exogenous sequence refers to a nucleic acid which is not naturally present in the parent virus.

An example of such a recombinant virus is JX-594/TG6006, which is thymidine kinase inactivated vaccinia virus (Wyeth strain), expressing an immune-stimulating cytokine which is a granulocyte macrophage colony stimulating factor, i.e. GM-CSF (see WO95/31105, WO2007/030668 and WO2008/113078). Another example is a doubly thymidine kinase (TK-) and ribonucleotide reductase (I4L-) inactivated vaccinia virus TG6002 (Copenhagen strain) expressing a suicide gene such as the FCU1 suicide gene (see WO2009/065546).

The exogenous sequence may also replace the function of a defective gene in the target cell. There are several thousand inherited genetic diseases of mammals, including humans, which are caused by defective genes such as for example diseases including cystic fibrosis, Duchenne muscular dystrophy or sickle cell disease. Many types of cancer are also caused by defective genes, especially protooncogenes, and tumour-suppressor genes that have undergone mutation, such as for example protooncogenes ras, src, bcl and so on. Examples of tumour-suppressor genes are p53 and Rb.

According to another possibility, the exogenous sequence can encode a Tumor Associated Antigen (TAA). TAA refers to a molecule that is detected at a higher frequency or density in tumor cells than in non-tumor cells of the same tissue type. Examples of TAA includes but are not limited to CEA, MART1, MAGE1, MAGE3, GP-100, MUC1, such as described in WO 92/07000, WO 95/09241 incorporated herein by reference, more preferably MUC1.

The exogenous gene may further encode an antigen. Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus (HBV) for example Hepatitis B Surface antigen or a derivative thereof (see WO2011/015656 and WO2013/007772), hepatitis A virus (HAV), hepatitis C virus (HCV; see WO 04/111082; preferentially non-structural HCV protein from genotype 1 b strain), and hepatitis E virus (HEV), or from other viral pathogens, such as Respiratory Syncytial Virus, Human Papilloma Virus (HPV; see WO 90/10459, WO 95/09241, WO 98/04705, WO 99/03885 and WO 07/121894; E6 and E7 protein from the HPV16 strain are preferred; see also Liu et al. Proc Natl Acad Sci USA. 2004 Oct. 5; 101 Suppl 2:14567-71) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*. According to the present invention, said antigen is more preferably selected from HCV or HPV. With this regard, such preferred recombinant virus used in a formulation according to the present invention is MVA-HCV (see WO 04/111082), also called TG4040 that is a MVA expressing HCV NS3, NS4 and NS5B antigens (NS3 and NS4 being expressed as a fusion protein and NS5B independently).

The recombinant virus can comprise more than one exogenous sequence and each exogenous sequence can encodes more than one molecule. For example, it can be useful to associate in a same recombinant virus, an exogenous sequenced encoding e.g. a TAA (as previously described) or an antigen (as previously described) with an exogenous sequence encoding a cytokine (e.g. interleukin (IL as for instance IL2); tumour necrosis factor (TNF); interferon-(IFN); colony stimulating factor (CSF)).

With this regard, preferred recombinant viruses used according to the present invention are:
MVA-[MUC1-IL2] that is a MVA expressing the MUC-1 antigen and IL-2 (see WO 92/07000 and WO 95/09241) also called TG4010; and
MVA-[HPV-IL2] that is a MVA expressing non oncogenic E6 and E7 antigens of HPV-16 and IL-2 (see WO 90/10459, WO 95/09241, WO 98/04705, WO 99/03885 and WO 07/121894) also called TG4001.

According to a preferred embodiment, a virus-based material of the present invention is a poxvirus-based product, more particularly a VV-based product such as the so called JX-594/TG6006 and TG6002 or a MVA-based product such as the so-called TG4040, TG4010 and TG4001.

The poxvirus contained in the formulation according to the present invention can be a naturally occurring poxvirus, an attenuated poxvirus or a recombinant poxvirus.

Methods for producing and purifying virus-based material, especially viral vectors and/or viruses used according to the present invention are known by the person skilled in the art. More particularly, concerning poxviruses, available production methods comprise the replication of the virus in a cell line (e.g. HelaS3 or a duck cell line), in embryonated eggs or in Chicken Embryo Fibroblasts (CEF). CEF cells are more particularly dedicated to produce MVA-based product. They can be cultivated under conditions known to the person skilled in the art. According to WO 07/147528, the virus produced from CEF or cell lines supernatant can be purified by depth filtration, microfiltration and diafiltration.

WO 2010/130753 describes a method for producing a poxvirus using nucleases and further purifying the virus using Anion Exchange Adsorbent.

Nevertheless, the results observed with the formulation of the Invention are obtained irrespectively of whether the virus in the formulation is an unpurified, purified or partially purified virus. Purified or partially purified viruses are preferred. "Purified" as used herein refers to a reduction of at least 90% of the protein content as compared to the protein content of the crude viral preparation whereas "partially purified" means a significant reduction (e.g. at least 20%) with respect to the protein content of the crude viral preparation.

According to one embodiment of the present invention, the said formulation comprises at least one virus-based material which is a virus and the virus titer in said formulation is comprised between $1 \cdot 10^6$ Pfu/mL and $1 \cdot 10^{10}$ Pfu/mL, more preferably between $1 \cdot 10^7$ Pfu/mL and $1 \cdot 10^9$ Pfu/mL, more preferably between $1 \cdot 10^7$ Pfu/mL and $5 \cdot 10^8$ Pfu/mL and more preferably between $1 \cdot 10^8$ Pfu/mL and $5 \cdot 10^8$ Pfu/m L.

The formulation of the Invention further comprises (ii) at least one polymer selected in the group of polyvinylpyrrolidone and derivatives thereof, and mixture thereof.

The term "polyvinylpyrrolidone" as used herein refers to a water-soluble polymer made from the monomer N-vinylpyrrolidone. The terms and abbreviations PVP, povidone, plasdone, polyvidone, crospovidone, kollidon are used synonymously.

As used herein, the term 'PVP derivatives' and variations thereof, is intended to mean substances comprising polyvinyl pyrrolidone (PVP) and substituted versions thereof, including, but not limited to: copovidone (for example, plasdone S-630 and kollidon VA-64; and cross-linked PVP (for example crospovidone also called polyvinylpolypyrrolidone or PVPP).

According to the present invention, PVP and derivatives thereof have a molecular weight, in the range of 5 kDa to 400 kDa, more preferably in a range of 5 kDa to 70 kDa. According to advantageous embodiment, PVP and derivatives thereof have a low molecular weight, i.e. a molecular weight of no more than 55 kDa, preferably comprised between 10 kDa and 40 kDa, preferably between 15 kDa and 30 kDa and which is more preferably of 25 kDa. At low molecular weight PVP polymer would be less immunogenic than at high MW and better tolerate during injection.

According to preferred embodiment, the formulation of the invention comprises between 5 g/L and 80 g/L of PVP or derivatives or mixture thereof, preferably between 10 g/L and 50 g/L, more preferably between 15 g/L and 40 g/L, and more preferably between 20 g/L and 35 g/L of PVP or derivatives thereof as above-defined. According to one specific embodiment, the formulation of the invention comprises 33.25 g/L of PVP, and more specifically of PVP having one molecular weight of 25 kDa.

The formulation of the Invention further comprises (iii) at least one sugar.

Said sugar is more preferably chosen among monosaccharide, disaccharide, trisaccharide and tetrasaccharide and derivatives thereof.

Monosaccharides such as glucose, galactose and mannose are preferably chosen according to the present invention.

Disccharrides according to the present invention are preferably chosen among sucrose (also named saccharose), lactulose, lactose, maltose, trehalose, cellobiose, isomaltose and maltulose.

Trisaccharide such as raffinose is preferably chosen according to the present invention.

Tetrasaccharide such as stachyose is also envisaged according to the present invention.

According to a preferred embodiment, a formulation of the present invention comprises at least one disaccharide. According to even more preferred embodiment, said disaccharide is selected in the group consisting of sucrose, lactulose, lactose, maltose, trehalose, cellobiose, isomaltose and maltulose and advantageously is sucrose.

According to preferred embodiment, the formulation of the invention comprises between 10 g/L and 100 g/L of sugar, preferably between 20 g/L and 80 g/L, more preferably between 30 g/L and 70 g/L and even more preferably between 40 g/L and 60 g/L. According to a more preferred embodiment of the present invention, said formulation comprises 50 g/L of sugar, advantageously 50 g/L of sucrose.

According to a preferred embodiment, a formulation of the present invention the weight ratio of sugar relative to PVP (sugar/PVP (w/w)) is at least 1, more preferably between 1 and 5, more preferably between 1 and 2 and is preferably 1.5.

The formulation of the Invention further comprises (iv) at least two different amino acids.

More preferably, said amino acids are chosen among alanine, arginine, asparagine, aspartate, cysteine, glutamine, glutamate, glycine, histidine, isoleucine, leucine, lysine, methionine, phenylalanine, proline, pyrrolysine, selenocysteine, serine, threonine, tryptophane, tyrosine and valine and derivatives thereof, including both stereoisomers.

Glutamate refers to the glutamic acid pharmaceutical acceptable salt form preferably it is a monovalent salt and more preferably a monosodium salt of glutamic acid, i.e. monosodium glutamate (MSG).

According to one preferred embodiment, a formulation of the present invention comprises at least one amino acid selected in the group consisting of L-stereoisomers, e.g. L-arginine.

According to one preferred embodiment, a formulation of the present invention comprises at least one amino acid selected in the group consisting of arginine, histidine and lysine.

According to another preferred embodiment, a formulation of the present invention comprises at least one amino acid selected in the group consisting of aspartate and glutamate.

According to a preferred embodiment, a formulation of the present invention comprises arginine and glutamate.

According to a preferred embodiment, the formulation of the Invention comprises total amounts of amino acid comprised between 10 g/L and 200 g/L, more preferably between 10 g/L and 150 g/L and more preferably between 10 g/L and 100 g/L.

According to another preferred embodiment, the formulation of the present invention comprises between 5 g/L and 100 g/L and more preferably between 5 g/L and 80 g/L of arginine. Concentration of arginine from 5 g/L to 20 g/L are more suited for virus formulation with a high viral titer (e.g. of about $1 \cdot 10^8$ PFU/mL or more) and higher concentration of arginine for virus formulation with a lower viral titer (e.g. less than $1 \cdot 10^8$ PFU/mL).

According to a more preferred embodiment, a formulation of the present invention comprises between 1 g/L and 50 g/L, more preferably between 1 g/L and 20 g/L, more preferably between 1 g/L and 10 g/L and more preferably between 1 g/L and 5 g/L of glutamate. According to a more preferred embodiment of the present invention, said formulation comprises 2.49 g/L of glutamate.

According to one specific embodiment of the present invention, said formulation comprises 2.49 g/L of glutamate and 8.43 g/L of arginine.

According to a more preferred embodiment of the present invention, said formulation comprises 2.49 g/L of glutamate and 42.13 g/L of arginine.

According to a more preferred embodiment of the present invention, said formulation comprises 2.49 g/L of glutamate and 56.04 g/L of arginine.

The formulation of the Invention further comprises (v) at least two pharmaceutical acceptable salts, wherein at least one of said salts is a phosphate salt.

Phosphates are known to cause pH shifts and their use in formulation has been considered as problematic (see for example: Freeze Drying of Pharmaceuticals & Biologicals Conference, Aug. 6-9, 2008, Great Divide Lodge Breckenridge, Colo.). Similarly, EP1418942 indicates that presence of phosphate in formulation containing virus based material, especially poxvirus, induces virus aggregation and precipitation, especially during drying process. Surprisingly, the Inventors of the present invention have shown that in the context of the present invention the phosphate buffer participate to the stabilizing properties of the claimed formulation.

According to one embodiment, at least one of the pharmaceutical acceptable salts of the invention is selected in the group consisting of sodium and potassium salts, and combination thereof.

According to preferred embodiment, at least one of the pharmaceutical acceptable salts of the formulation is a phosphate salt and is selected in the group consisting of monobasic phosphate salts, dibasic phosphate salts and tribasic phosphate salts.

According one embodiment, at least one of the pharmaceutical acceptable salts of the formulation is a phosphate salt and is selected in the group consisting of monosodium phosphate (NaH$_2$PO$_4$) and monopotassium phosphate (KH$_2$PO$_4$).

According another embodiment, at least one of the pharmaceutical acceptable salts of the formulation is a phosphate salt and is selected in the group consisting of disodium phosphate (Na$_2$HPO$_4$) and dipotassium phosphate (K$_2$HPO$_4$)

According another embodiment, at least one of the pharmaceutical acceptable salts of the formulation is a phosphate salt and is selected in the group consisting of tripotassium phosphate (K$_3$PO$_4$) and trisodium phosphate (Na$_3$PO$_4$), According to one preferred embodiment of the present invention, at least one of the pharmaceutical acceptable salts of the formulation is disodium phosphate Na$_2$HPO$_4$.

According to another embodiment, a formulation according to the present invention comprises (v) at least two phosphate salts which form a phosphate buffer. Said phosphate buffer is more preferably a mixture comprising at least one monobasic phosphate salt and at least one dibasic phosphate salt. Said phosphate buffer is more preferably a mixture comprising dipotassium phosphate (KH$_2$PO$_4$) and disodium phosphate (Na$_2$HPO$_4$). Thus according to one preferred embodiment, the formulation of the present invention comprises (v) dipotassium phosphate (KH$_2$PO$_4$) and disodium phosphate (Na$_2$HPO$_4$).

According to one specific embodiment, the formulation of the present invention comprises (v) dipotassium phosphate (KH$_2$PO$_4$) and disodium phosphate (Na$_2$HPO$_4$) in ratio of about 1:5, respectively.

According to another preferred embodiment, the formulation of the Invention comprises at least 0.1 g/L, more preferably between 0.1 g/L and 10 g/L and even more preferably between 0.1 g/L and 5 g/L of phosphate salt.

According to one specific embodiment of the present invention, said formulation comprises at least 0.1 g/L, preferably 0.19 g/L of phosphate salt.

According to another preferred embodiment, the formulation of the Invention comprises at least 0.1 g/L of Na$_2$HPO$_4$, and preferably between 0.1 g/L and 5 g/L of Na$_2$HPO$_4$.

According to one specific embodiment of the present invention, said formulation comprises 0.19 g/L of phosphate salt, and even more specifically 0.19 g/L of Na$_2$HPO$_4$.

According to another preferred embodiment, the formulation of the Invention comprises at least 0.1 g/L of KH$_2$PO$_4$, preferably between 0.1 g/L and 5 g/L of KH$_2$PO$_4$, even preferably between 0.1 g/L and 1 g/L of KH$_2$PO$_4$, and more preferably between 0.1 g/L and 0.6 g/L of KH$_2$PO$_4$.

According to another specific embodiment of the present invention, said formulation comprises 0.94 g/L of phosphate salt, and even more specifically 0.79 g/L of Na$_2$HPO$_4$. and 0.15 g/L of KH$_2$PO$_4$.

According to another specific embodiment of the present invention, said formulation comprises 1.88 g/L of phosphate salt, and even more specifically 1.59 g/L of Na$_2$HPO$_4$. and 0.29 g/L of KH$_2$PO$_4$.

According to another specific embodiment of the present invention, said formulation comprises 3.75 g/L of phosphate salt, and even more specifically 3.17 g/L of Na$_2$HPO$_4$. and 0.58 g/L of KH$_2$PO$_4$.

In the context of the invention, it is preferred that said formulation comprises at least 1 g/L of phosphate buffer (e.g. at least 1.2, 1.5, 1.6, 1.7 or 1.8 g/L). A preferred formulation comprises both phosphate buffer as defined above (e.g. 1.59 g/L of Na$_2$HPO$_4$. and 0.29 g/L of KH$_2$PO$_4$ or 3.17 g/L of Na$_2$HPO$_4$. and 0.58 g/L of KH$_2$PO$_4$) and arginine as defined above (e.g. about 8.43 g/L or more).

According to another specific embodiment, the formulation of the Invention comprises (v) at least one additional pharmaceutical acceptable salt, which is not a phosphate salt.

According to one embodiment, said additional pharmaceutical acceptable salt is a monovalent salt. According to one preferred embodiment said additional pharmaceutically acceptable salt is selected in the group consisting of NaCl and KCl, and is preferably NaCl.

According to one embodiment, the formulation of the invention comprises between 1 g/L and 10 g/L, preferably no more than 5 g/L and more preferably between 1 g/L and 5 g/L of said additional pharmaceutical acceptable salt.

According to one specific embodiment of the present invention, said formulation comprises 3.89 g/L of NaCl.

According to one specific embodiment of the present invention, said formulation comprises 1.94 g/L of NaCl.

The formulation of the Invention may further comprise (vi) a pharmaceutical acceptable buffer.

According to one embodiment, the formulation of the Invention further comprises a pharmaceutical acceptable buffer.

According to one embodiment, the pH of a formulation according to the present invention is comprised between about 7 and about 8.5, preferably is 7.5±0.5 and more preferably is 7.5. The pH can be adjusted with the respective amounts of the phosphate salts, more preferably KH$_2$PO$_4$ and Na$_2$HPO$_4$, according to well-known methods of the person skilled in the art such as in Sorensen in Hayat, 1986.

The said pharmaceutical acceptable buffer can be selected in the group consisting in TRIS, BES, TES, DIPSO, MOBS, TAPSO, HEPPSO, POPSO, MOPS, HEPES and bicarbonates. According to a preferred embodiment, said buffer is TRIS or HEPES, and even more preferably is TRIS.

According to one preferred embodiment, the formulation of the invention comprises between about 1 mM and about 100 mM and more preferably between about 1 mM and about 50 mM of said pharmaceutical acceptable buffer.

According to one specific embodiment of the present invention, said formulation comprises about 10 mM of TRIS, more specifically 1.61 g/L of TRIS.

According to advantageous embodiment, the present invention relates to a formulation comprising (i) at least one virus-based material, (ii) at least one polymer selected in the group of polyvinylpyrrolidone and derivatives thereof, (iv) at least two different amino acids, (v) at least two pharmaceutical acceptable salts, wherein at least one of said salts is a phosphate salt and wherein said phosphate salt is a disodium phosphate salt, and optionally (vi) a pharmaceutical acceptable buffer which is more preferably chosen among TRIS or HEPES According to advantageous embodiment, the present invention relates to a formulation comprising (i) at least one virus-based material, (ii) at least one polymer selected in the group of polyvinylpyrrolidone and derivatives thereof, (iv) at least two different amino acids, (v) a mixture of disodium phosphate salt and monopotassium phosphate salt, and optionally (vi) a pharmaceutical acceptable buffer which is more preferably chosen among TRIS or HEPES According to advantageous embodiment, the present invention relates to a formulation comprising (i) at least one virus-based material, (ii) at least one polymer selected in the group of polyvinylpyrrolidone and derivatives thereof, (iv) at least two different amino acids, (v) a mixture of disodium phosphate salt, monopotassium phosphate salt and NaCl, and optionally (vi) a pharmaceutical acceptable buffer which is more preferably chosen among TRIS or HEPES According to advantageous embodiment, the present invention relates to a formulation comprising (i) a poxvirus, (ii) PVP, (iii) sucrose, (iv) arginine and glutamate, (v) at least two pharmaceutical acceptable salts, wherein at least one of said salts is a phosphate salt and optionally (vi) a pharmaceutical acceptable buffer.

According to another advantageous embodiment, the present invention relates to a formulation comprising (i) a poxvirus, (ii) PVP, (iii) sucrose, (iv) arginine and glutamate, (v) a mixture of at least one monovalent phosphate salt and/or at least one one divalent phosphate salt, and optionally (v) a pharmaceutical acceptable buffer.

According to another advantageous embodiment, the present invention relates to a formulation comprising (i) a poxvirus, (ii) PVP, (iii) sucrose, (iv) arginine and glutamate, (v) a mixture of disodium phosphate salt and monopotassium phosphate salt, and optionally (vi) a pharmaceutical acceptable buffer.

According to advantageous embodiment, the present invention relates to a formulation comprising (i) a poxvirus, (ii) PVP, (iii) sucrose, (iv) arginine and glutamate, (v) at least one phosphate salt and at least one monovalent salt, preferably NaCl, and optionally (vi) a pharmaceutical acceptable buffer.

According to another advantageous embodiment, the present invention relates to a formulation comprising (i) a poxvirus, (ii) PVP, (iii) sucrose, (iv) arginine and glutamate, (v) at least one monovalent phosphate salt and/or at least one divalent phosphate salt and at least one one monovalent salt, preferably NaCl, and optionally (v) a pharmaceutical acceptable buffer.

According to advantageous embodiment, the present invention relates to a formulation comprising (i) a poxvirus, (ii) PVP, (iii) sucrose, (iv) arginine and glutamate, (v) disodium phosphate salt and at least one monovalent salt, preferably NaCl, and optionally (vi) a pharmaceutical acceptable buffer.

According to advantageous embodiment, the present invention relates to a formulation comprising (i) a poxvirus, (ii) PVP, (iii) sucrose, (iv) arginine and glutamate, (v) a mixture of disodium phosphate salt and monopotassium phosphate and at least one monovalent salt, preferably NaCl, and optionally (vi) a pharmaceutical acceptable buffer.

According to advantageous embodiment, the present invention relates to a formulation comprising (i) a poxvirus selected in the group consisting of MVA and VV, (ii) PVP, (iii) sucrose, (iv) arginine and glutamate, (v) at least two pharmaceutical acceptable salts, wherein at least one of said salts is a phosphate salt and optionally (vi) a pharmaceutical acceptable buffer.

According to another advantageous embodiment, the present invention relates to a formulation comprising (i) a poxvirus selected in the group consisting of MVA and VV, (ii) PVP, (iii) sucrose, (iv) arginine and glutamate, (v) a mixture of at least one monovalent phosphate salt and/or at least one one divalent phosphate salt, and optionally (v) a pharmaceutical acceptable buffer.

According to another advantageous embodiment, the present invention relates to a formulation comprising (i) a poxvirus selected in the group consisting of MVA and VV, (ii) PVP, (iii) sucrose, (iv) arginine and glutamate, (v) a mixture of disodium phosphate salt and monopotassium phosphate salt, and optionally (vi) a pharmaceutical acceptable buffer.

According to advantageous embodiment, the present invention relates to a formulation comprising (i) a poxvirus selected in the group consisting of MVA and VV, (ii) PVP, (iii) sucrose, (iv) arginine and glutamate, (v) at least one phosphate salt and one monovalent salt, preferably NaCl, and optionally (vi) a pharmaceutical acceptable buffer.

According to advantageous embodiment, the present invention relates to a formulation comprising (i) a poxvirus selected in the group consisting of MVA and VV, (ii) PVP, (iii) sucrose, (iv) arginine and glutamate, (v) disodium phosphate salt and at least one monovalent salt, preferably NaCl, and optionally (vi) a pharmaceutical acceptable buffer.

According to advantageous embodiment, the present invention relates to a formulation comprising (i) a poxvirus selected in the group consisting of MVA and VV, (ii) PVP, (iii) sucrose, (iv) arginine and glutamate, (v) a mixture of disodium phosphate salt and monopotassium phosphate and at least one monovalent salt, preferably NaCl, and optionally (vi) a pharmaceutical acceptable buffer.

According to another advantageous embodiment, the present invention relates to a formulation comprising (i) a poxvirus, (ii) PVP, (iii) sucrose, (iv) arginine and glutamate, (v) a mixture of disodium phosphate salt and monopotassium phosphate salt, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus, (ii) PVP, (iii) sucrose, (iv) arginine and glutamate, (v) at least one phosphate salt and one monovalent salt, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus, (ii) PVP, (iii) sucrose, (iv) arginine and glutamate, (v) disodium phosphate salt and at least one monovalent salt, preferably NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus, (ii) PVP, (iii) sucrose, (iv) arginine and glutamate, (v) a mixture of disodium phosphate salt and monopotassium phosphate and at least one monovalent salt, preferably NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus, (ii) PVP, (iii) sucrose, (iv) arginine and glutamate, (v) a mixture of disodium phosphate salt and monopotassium phosphate and NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus selected in the group consisting of MVA and VV, (ii) PVP, (iii) sucrose, (iv) arginine and glutamate, (v) at least two pharmaceutical acceptable salts, wherein at least one of said salts is a phosphate salt and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to another advantageous embodiment, the present invention relates to a formulation comprising (i) a poxvirus selected in the group consisting of MVA and VV, (ii) PVP, (iii) sucrose, (iv) arginine and glutamate, (v) a mixture of at least one monovalent phosphate salt and/or at least one divalent phosphate salt, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to another advantageous embodiment, the present invention relates to a formulation comprising (i) a poxvirus selected in the group consisting of MVA and VV, (ii) PVP, (iii) sucrose, (iv) arginine and glutamate, (v) a mixture of disodium phosphate salt and monopotassium phosphate salt, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus selected in the group consisting of MVA and VV, (ii) PVP, (iii) sucrose, (iv) arginine and glutamate, (v) at least one phosphate salt and one monovalent salt, preferably NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus selected in the group consisting of MVA and VV, (ii) PVP, (iii) sucrose, (iv) arginine and glutamate, (v) disodium phosphate salt and at least one monovalent salt, preferably NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus selected in the group consisting of MVA and VV, (ii) PVP, (iii) sucrose, (iv) arginine and glutamate, (v) a mixture of disodium phosphate salt and monopotassium phosphate and at least one monovalent salt, preferably NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to advantageous embodiment, the present invention relates to a formulation comprising (i) a poxvirus selected in the group consisting of MVA and VV, (ii) PVP, (iii) sucrose, (iv) arginine and glutamate, (v) a mixture of disodium phosphate salt and monopotassium phosphate and NaCl, and (vi) a pharmaceutical acceptable buffer selected in the group of TRIS, BES, TES, DIPSO, MOBS, TAPSO, HEPPSO, POPSO, MOPS, HEPES and bicarbonates, preferably TRIS buffer.

According to another advantageous embodiment, the present invention relates to a formulation comprising (i) a poxvirus selected in the group consisting of MVA and VV, (ii) PVP, (iii) sucrose, (iv) arginine and glutamate, (v) from about 0.1 g/L to about 1 g/L of disodium phosphate salt and from about 1 g/L to about 10 g/L, preferably from about 1 g/L to about 5 g/L of monovalent salt, preferably NaCl.

According to another advantageous embodiment, the present invention relates to a formulation comprising (i) a poxvirus selected in the group consisting of MVA and VV, (ii) PVP, (iii) sucrose, (iv) arginine and glutamate, (v) from about 0.1 g/L to about 1 g/L of disodium phosphate salt and from about 1 g/L to about 10 g/L, preferably from about 1 g/L to about 5 g/L of monovalent salt, preferably NaCl, and (vi) from about 1 g/L to about 10 g/L and more preferably from about 1 g/L to about 5 g/L of TRIS buffer.

A typical virus containing formulation suitable for freeze drying comprises (ii) 33.25 g/L of PVP 25 kDa, (iii) 50 g/L of sucrose, (iv) 2.49 g/L of glutamate and 8.43 g/L of arginine, (v) 0.79 g/L of $Na_2HPO_4$. and 0.15 g/L of $KH_2PO_4$.

According to another specific embodiment of the present invention, said formulation comprises 1.88 g/L of phosphate salt, and even more specifically 1.59 g/L of $Na_2HPO_4$. and 0.29 g/L of $KH_2PO_4$.

According to another specific embodiment of the present invention, said formulation comprises 3.75 g/L of phosphate salt, and even more specifically 3.17 g/L of $Na_2HPO_4$. and 0.58 g/L of $KH_2PO_4$.

According to another specific embodiment of the present invention, said formulation comprises 3.89 g/L of NaCl.

According to one specific embodiment of the present invention, said formulation comprises 1.94 g/L of NaCl.

According to another specific embodiment of the present invention, said formulation comprises 3.89 g/L of NaCl and 1.61 mM of TRIS.

According to one specific embodiment of the present invention, said formulation comprises 1.94 g/L of NaCl and 1.61 g/L of TRIS.

Dry Product

The present invention further concerns a stable virus-based material containing vaccine which comprises the formulation as disclosed above in dried, preferably freeze dried form.

The term "dry" denotes a formulation, composition, product, vaccine and the like which exhibits a residual moisture content of less than 3% by weight of product preferably less than 2% and more preferably of 1% or less. According to particular embodiment, the dried material (including dry formulation, dry composition, dry product, dry vaccine, dry virus-based material containing vaccine) is solid either in crystalline or amorphous form both at about 5° C., room temperature and until about 45° C.

According to one specific embodiment, said residual moisture content is determined by Karl Fisher method.

According to the present invention, "dry material" (including dry formulation, dry composition, dry product, dry vaccine, dry virus-based material containing vaccine) has a residual moisture such as above defined.

According to one embodiment, said dry material can be obtained by freeze-drying a formulation, preferably aqueous formulation, as above disclosed. Thus, according to preferred embodiment, a dry material (particularly dry formulation or dry virus-based material containing vaccine of the present invention) refers to a "freeze-dried" or "lyophilized" material (particularly "freeze-dried" or "lyophilized" formulation, or "freeze-dried" or "lyophilized" virus-based material containing vaccine of the present invention).

The terms "freeze-dried" and "lyophilized" are equivalent, as well as the terms "lyophilization" and "freeze-drying".

According to preferred embodiment, the loss in virus titer after lyophilization, i.e. loss due to freeze-drying process, is no more than 0.3 log, preferably no more than 0.2 log and more preferably no more than 0.1 log.

Furthermore, said "dry material" is advantageously stable (see below), i.e. its cumulated loss in virus titer is limited.

Furthermore, it has to be noted that, whereas it is known in the literature that phosphate salts such as disodium hydrogen phosphate dodecahydrate ($Na_2HPO_4$, [$12H_2O$]), precipitate at low temperatures, thereby possibly lowering the pH of the product dramatically (Croyle et al., «Factors that influence stability of recombinant adenoviral preparations for human gene therapy, Pharmaceutical development and technology», 3(3), 373-383, 1998), the pH of formulation according to the present invention was unexpectedly maintained during freezing at all temperatures.

It is further desired that "dry material" according to the present invention have a low residual moisture (RM) content, since it is known by the person skilled in the art to be an indicator of stability as exposure to moisture during storage can destabilize a product and thus allowing lower preservation term. RM is the amount of bound water that remains in a freeze-dried product. The well-known colorimetric Karl Fisher Technique for testing residual moisture can be used in order to determine water content by volumetric titration (Jennings, T. A., "Lyophilization, Introduction and Basic Principles", Interpharm Press, Denver, Colo., US, 1999, ISBN 1-57491-081-7, pages 415-418). This is measured as the weight percentage of water remaining compared to the total weight of the dried product. The European Pharmacopea (V Edition) recommends a RM below 3% by weight of product.

More particularly, in "dry material" according to the present invention, the RM is less than 3% by weight of product, more preferably less than 2% and is more preferably 1% by weight of product or below.

It is also expected that "dry material" according to the present invention show a convenient aspect. Actually, suitable dry compositions present a smooth, white layer or "cake" which is not retracted from the sides of the vial after lyophilization. Less suitable "dry material" appears "melted", "boiled" or otherwise malformed, and retracted from the sides of the vial after storage.

The "dry material" can be obtained in a dry powder form. A cake resulting from e.g. freeze-drying can be milled into powder form. A solid "dry material" according to the invention may thus take the form of free-flowing particles. The solid composition is typically provided as a powder in a sealed vial, ampoule or syringe. The solid matrix can alternatively be provided as a patch. A powder may be compressed into tablet form.

Freeze-Drying Process

As above mentioned, the formulation, preferably aqueous formulation, of the invention is suitable for drying, preferably freeze-drying. Preferably, the virus-based material comprised in the formulation subject to freeze drying is purified or at least partially purified as defined above.

According to one special embodiment, the present invention relates to a method for the preparation of "dry material" wherein said method comprises the step of freeze-drying an aqueous formulation comprising (i) at least one virus-based material, (ii) at least one polymer selected in the group of polyvinylpyrrolidone and derivatives thereof, (iii) at least one sugar, (iv) at least two different amino acids, (v) at least two pharmaceutical acceptable salts, wherein at least one of said salts is a phosphate salt and, optionally (vi) a pharmaceutical acceptable buffer.

Methods of freeze-drying are generally known by the person skilled in the art (Day, J. and McLellan, M., Methods in Molecular Biology, Humana Press, (1995) vol. 38).

There are usually three main stages to the freeze-drying method namely freezing, primary drying and secondary drying. Freezing is typically performed using a freeze-drying machine. During this step, it is important to cool the biological material below its eutectic point, (Teu) in the case of simple crystalline products or glass transition temperature (Tg') in the case of amorphous products, i.e. below the lowest temperature at which the solid and liquid phase of the material can coexist. This ensures that sublimation rather than melting will occur in the following primary drying stage.

During primary drying, the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

In the context of the present invention, it has been surprisingly found that high temperatures, i.e. up to 50° C. could be applied to the secondary drying step in order to fasten the freeze-drying process, without impairing the virus.

Thus, the present invention more preferably relates to a freeze-drying process, consisting in drying a liquid composition according to the present invention and wherein the secondary drying step is performed at a temperature varying up to 50° C.±5° C., more preferably between 30° C. and 45° C. and is preferably performed at 40° C.±5° C.

Furthermore, it is to be noted that a dry product with the same titer parameters could be produced in a volume being reduced, for example to one third that of the fill volume, thus allowing increasing the concentration of one third and further decreasing the duration of the lyophilization cycle compared to what is usually known in the art for viruses such as poxviruses.

Reconstituted Material

The present invention further concerns reconstituted material. "Reconstituted material" (including reconstituted formulation, reconstituted composition, reconstituted product, reconstituted vaccine, reconstituted virus-based material containing vaccine) corresponds to a "dry material" (including dry formulation, dry composition, dry product, dry vaccine, dry virus-based material containing vaccine) which has been reconstituted by the addition of suitable amount of pharmaceutically acceptable solvent. According to special embodiment, the pharmaceutically acceptable solvent is selected in the group consisting of water for injection (WFI), physiological serum or saline solutions such as NaCl solution.

When the formulation according to the present invention, was containing additional salt, more preferably monovalent salt such as NaCl, is more particularly dedicated to adjust, if necessary, the osmolality of the reconstituted material. More precisely, osmolality of a reconstituted material according to the present invention shall be compatible with injection use, i.e. shall be comprised between 280 mOsm/kg and 900 mOsm/kg, more particularly between 280 mOsm/kg and 600 mOsm/kg and more preferably between 280 mOsm/kg and 350 mOsm/kg.

Viral Titer

One of the major drawbacks of drying process, and more particularly freeze-drying process, is that they can be unstable, leading to an overall virus titer loss in virus which can be increased during storage.

One aim of the present Invention was to provide formulation, preferably aqueous formulation, which is stable. It further relates to dry, preferably freeze-dried, formulation as disclosed above that is stable. More particularly, said stability means that virus-based material or product contained in the formulation (including aqueous or dry form) of the Invention is biologically active and retains its biological activity (i.e. the virus-based material, for example poxvirus, remains infectious) when formulated according to the Invention. According to the Invention, the virus-based material retains its biological activity when formulated according to the Invention, if the biological activity of the virus-based material at a given time is within about 10% (within the errors of the assay) of the biological activity exhibited at the time the formulation was prepared. In the case of viruses, biological activity can be considered retained when the viral titer of the formulation is within one log of the initial titer. According to particular embodiment, the virus-based material containing formulation of the present Invention is stable when the overall loss in virus titer at an incubation temperature of +5° C.+/−3° C. during at least 60 days (e.g. 90 days or even more such as several months or years) is less than 0.7 logs, preferably less than 0.5 logs, more preferably less than 0.4 logs and even more preferably less than 0.3 log.

The "overall loss in virus titer" according to the present invention is defined as the cumulated loss in virus titer measured after drying step and measured during storage of the dry formulation (measurement are performed after reconstitution of the material into water).

The "loss in virus titer after drying step" corresponds to the loss of virus titer between the time the formulation was prepared and after the drying step, i.e. it is the loss in virus titer due to drying process as such. In the following experiments, it corresponds to the loss in virus titer measured at day 0 versus day −1 (see Examples Section).

The "loss in virus titer after drying step" is temperature independent and is preferably less than 0.3 log, more preferably less than 0.2 log.

The "loss in virus titer during storage" of said dry formulation corresponds to the loss of virus titer after drying step and during a determined storage period of "n" days at a determined storage temperature.

The "loss in virus titer during storage" is preferably less than 0.4 log at +5° C.+/−3° C. for at least 60 days, more preferably less than 0.3 log at +5° C.+/−3° C. for at least 60 days (e.g. 90 days or even more).

Alternatively, it is possible to shorten the stability evaluation of formulations according to the present invention by performing accelerated stability studies at elevated temperatures. Actually, such accelerated stability studies allow predicting the results at lower temperature, without having to wait for real time stability data, i.e. generally 1-3 years at +5° C.+/−3° C. (versus e.g. about 1 week at 37+/−5° C. and about 3-5 days at 45+/−5° C.). For this purpose, different mathematical models are described in the state of the art and can be used in order to extrapolate results at lower temperatures. One of these models is the well-known order is Arrhenius principle-based multivariate model, which read as follows:

$$\ln\left(\ln\left(\frac{C_0}{C}\right)\right) = \beta_0 + \beta_1 * \frac{1}{T} + \beta_2 * \ln(t)$$

wherein $C_0$ is the initial titer in PFU/mL, T is the temperature in Kelvin degrees, t is the time in days, C is the titer at the corresponding time t in PFU/mL and $\beta_0$, $\beta_1$ and $\beta_2$ are parameters of the model (which can vary, depending on the specific data of the model).

Usually, accelerated stability tests are performed during about 1 week at 37+/−5° C. (World Health Organization recommendation). In the present case, such accelerated studies have been performed at 45+/−5° C. at different time periods (See Examples section).

"Room Temperature" (RT) as used in the present specification corresponds to a temperature comprised between about 20° C. and about 25° C.

The assay that is used to determine poxvirus titer for example is the plaque assay technique (see for example, Kaufmann and Kabelitz, 2002, Methods in Microbiology Vol. 32: Immunology of Infection. Academic Press. ISBN 0125215320). The titer from this assay is reported as Plaque Forming Unit per milliliter (PFU/mL). A detailed protocol to determine the virus titer and thus the overall, loss in virus titer is given in the example section. However, any alternate protocol to determine the viral titer can also be used.

The formulation comprising the virus-based material or the reconstituted material according to the Invention, may be administered to a patient or an animal in need thereof, more particularly as a vaccine for a therapeutic or prophylactic use.

According to another embodiment, the invention concerns a formulation comprising the virus-based material or a reconstituted material as previously defined for use as a vaccine. It may be administered by different routes, which may be for instance the intravenous, intratumor, intramuscular, intradermal, subcutaneous or intraperitoneal route. It is within the skills of the practitioner how such a formulation, in particular an aqueous formulation containing poxviruses can be administered properly. The administration may be made as a single dose or repeated once or several times after a certain time interval. The appropriate route of administration and dosage vary as a function of various parameters, for example, of the individual, of the disease to be treated or of the gene(s) of interest to be transferred.

The present invention also relates to a method for administering a formulation comprising the virus-based material or a reconstituted material as previously defined to a host in need thereof, characterized in that a dry product is reconstituted in a physiologically acceptable solvent, preferably chosen among water PPI, WFI, physiological serum or saline solution such as a NaCl solution, and then administered to said host in need thereof.

The present invention also relates to a formulation comprising the virus-based material or a reconstituted material as previously defined, for the treatment and/or the prevention of diseases and more preferably of disease conditions chosen among cancers, infectious diseases and/or autoimmune disorders.

As used herein, "cancer" refers but is not limited to lung cancer (e.g. small cell lung carcinomas and non-small cell lung), bronchial cancer, oesophageal cancer, pharyngeal cancer, head and neck cancer (e.g. laryngeal cancer, lip cancer, nasal cavity and paranasal sinus cancer and throat cancer), oral cavity cancer (e.g. tongue cancer), gastric cancer (e.g. stomach cancer), intestinal cancer, gastrointestinal cancer, colon cancer, rectal cancer, colorectal cancer, anal cancer, liver cancer, pancreatic cancer, urinary tract cancer, bladder cancer, thyroid cancer, kidney cancer, carcinoma, adenocarcinoma, hepatocarcinoma, hepatocellular carcinoma (HCC) or metastatic colorectal cancer (mCRC), skin cancer (e.g. melanoma), eye cancer (e.g. retinoblastoma), brain cancer (e.g. glioma, medulloblastoma and cerebral astrocytoma), central nervous system cancer, lymphoma (e.g. cutaneous B-cell lymphoma, Burkitt's lymphoma, Hodgkin's syndrome and non-Hodgkin's lymphoma), bone cancer, leukaemia, breast cancer, genital tract cancer, cervical cancer (e.g. cervical intraepithelial neoplasia), uterine cancer (e.g. endometrial cancer), ovarian cancer, vaginal cancer, vulvar cancer, prostate cancer, testicular cancer. "Cancers" also refer to virus-induced tumors, including, but is not limited to papilloma virus-induced carcinoma, herpes virus-induced tumors, EBV-induced B-cell lymphoma, hepatitis B-induced tumors, HTLV-1-induced lymphoma and HTLV-2-induced lymphoma.

In case of cancers, such administration of a composition according to the present invention may further be associated with a first line chimiotherapy.

As used herein, "infectious disease" refers to any disease that is caused by an infectious organism. Infectious organisms include, but are not limited to, viruses (e.g. single stranded RNA viruses, single stranded DNA viruses, human immunodeficiency virus (HIV), hepatitis A, B, and C virus, herpes simplex virus (HSV), cytomegalovirus (CMV), respiratory syncytial virus (RSV), Epstein-Barr virus (EBV) or human papilloma virus (HPV)), parasites (e.g. protozoan and metazoan pathogens such as Plasmodia species, *Leishmania* species, *Schistosoma* species or *Trypanosoma* species), bacteria (e.g. *Mycobacteria* in particular, *M. tuberculosis, Salmonella*, Streptococci, *E. coli* or Staphylococci), fungi (e.g. *Candida* species or *Aspergillus* species), *Pneumocystis carinii*, and prions.

As used herein, "autoimmune disorder" refers to two general types: 'Systemic autoimmune diseases' (i.e., disorders that damage many organs or tissues), and 'localized autoimmune diseases' (i.e., disorders that damage only a single organ or tissue). However, the effect of 'localized autoimmune diseases', can be systemic by indirectly affecting other body organs and systems. 'Systemic autoimmune diseases' include but are not limited to rheumatoid arthritis which can affect joints, and possibly lung and skin; lupus, including systemic lupus erythematosus (SLE), which can affect skin, joints, kidneys, heart, brain, red blood cells, as well as other tissues and organs; *scleroderma*, which can affect skin, intestine, and lungs; Sjogren's syndrome, which can affect salivary glands, tear glands, and joints; Goodpasture's syndrome, which can affect lungs and kidneys; Wegener's granulomatosis, which can affect sinuses, lungs, and kidneys; polymyalgia rheumatica, which can affect large muscle groups, and temporal arteritis/giant cell arteritis, which can affect arteries of the head and neck. 'Localized autoimmune diseases' include but are not limited to Type 1 Diabetes Mellitus, which affects pancreas islets; Hashimoto's thyroiditis and Graves' disease, which affect the thyroid; celiac disease, Crohn's diseases, and ulcerative colitis, which affect the gastrointestinal tract; multiple sclerosis (MS) and Guillain-Barre syndrome, which affect the central nervous system; Addison's disease, which affects the adrenal glands; primary biliary sclerosis, sclerosing cholangitis, and autoimmune hepatitis, which affect the liver; and Raynaud's phenomenon, which can affect the fingers, toes, nose, ears.

Thus, the present invention further relates to a method for treating or preventing disease conditions as mentioned above using a formulation comprising the virus-based material or a reconstituted material as previously defined. Such a method more preferably comprises reconstituting a lyophilized product as defined above, and administering the corresponding reconstituted material to a host in need thereof.

Then, another embodiment of the present invention concerns a method for the vaccination of an animal, including a human, in need thereof, with a formulation comprising the virus-based material or a reconstituted material as previously defined.

If necessary, the composition of the invention may further be formulated with conventional vaccine vehicles which are well known by the person skilled in the art.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

Unless otherwise specified, all the materials used in order to achieve the following examples are commercially available.

DESCRIPTION OF THE DRAWINGS

FIG. 1 illustrates the cumulative loss of infectious titer of a MVA vector (TG4001) formulated in the absence of phosphate (back bars) or in the presence of increasing concentrations of phosphate (light grey to dark grey) and stored at 5° C.

EXAMPLES

Figure 1A:
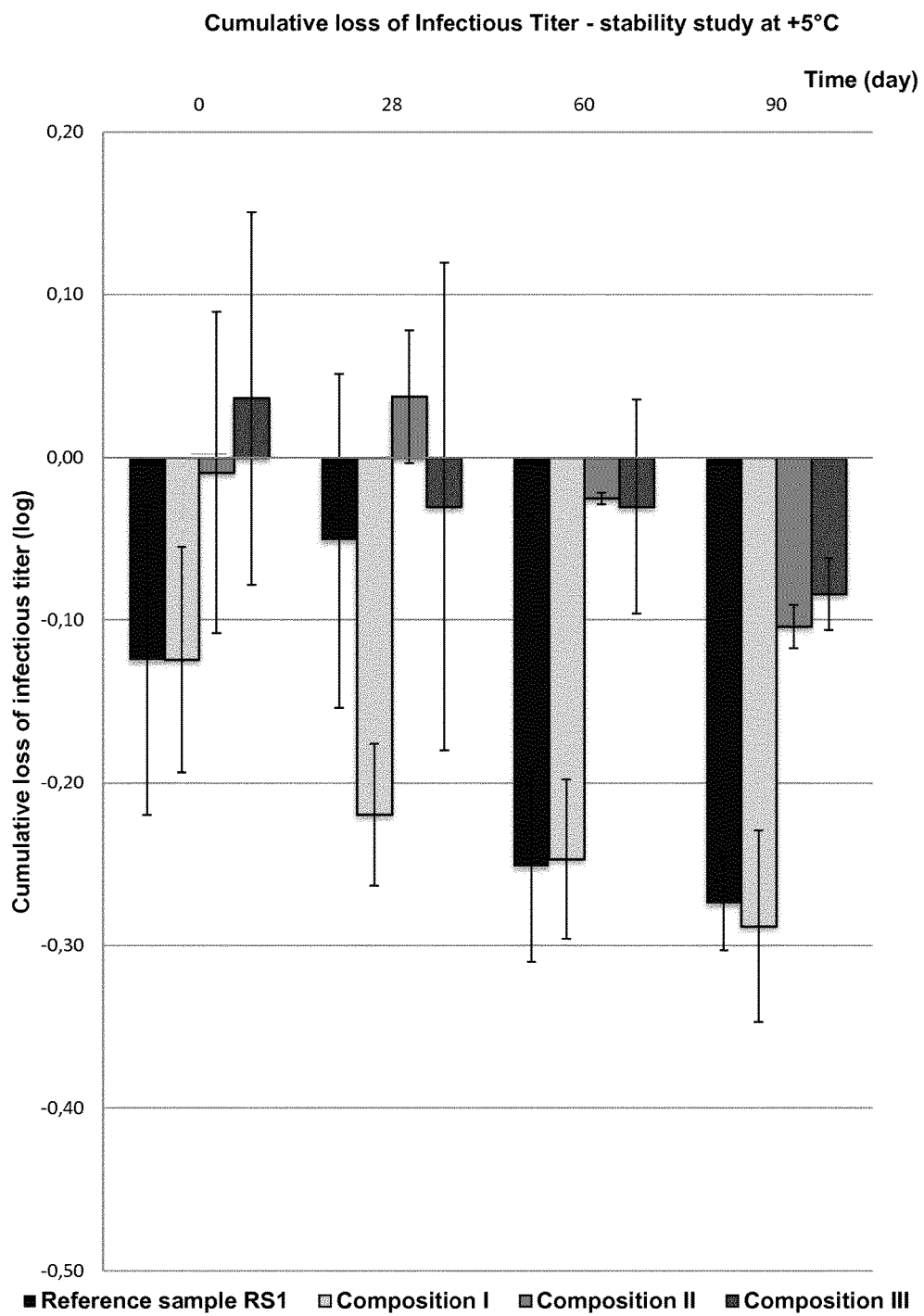
(FIG. 1A) or 45° C.

Material
   L-Arginine hydrochloride Powder (J.T BACKER—SIGMA);
   SVF (PAA)
   TRIS=TRIS (hydroxymethyl)aminomethane Powder (J.T BACKER);
   Hydrochloric acid (HCl) 1M (MERCK);
   Sodium hydroxyde (NaOH) 1N (VWR);
   Sucrose Powder (MERCK);
   Sodium chloride (NaCl) Powder (MERCK);
   PVP25 Powder (MERCK);
   L-Glutamic Acid monosodium salt (MERCK);
   di-Sodium Hydrogen Phosphate, Anhydrous Powder (MERCK);
   Potassium Dihydrogen Phosphate Anhydrous Powder (MERCK);
   Water for injection (COOPER);
   Vials=TopLyo® vials (SCHOTT); Stoppers (STELMI);
   DAB=3,3'-diaminobenzidine (SIGMA);

Host cells BHK-21 (ATCC, CCL10);
Anti-vaccine antibody (Meridian Life science);
Anti-rabbit antibody combined with peroxidase (DAKO);
Water MilliQ (Millipore);
PBS (DULBECCO SIGMA);
Triton X-100 (SIGMA);
DMEM (GIBCO)
Cations 100× (10 g/L Magnesium acetate tetrahydrate MERCK and 10 g/L Calcium chloride dihydrate JT BAKER);

It is to be noted that in the following tables, when "-" is indicated, it means that the corresponding ingredient is not present in the corresponding compositions.

Method

The viral titration method in order to evaluate the stability of formulation according to the present invention during lyophilization and during storage overtime is detailed hereinafter.

Some dry samples were reconstituted and titrated immediately after lyophilization to evaluate the effect of the lyophilization process on virus stability (i.e. virus titer loss at day 0 in the following examples).

Other dry samples were stored after lyophilization at different temperatures (for instance at 5° C. and 45° C.) until reconstitution for titration to evaluate the virus titer loss during storage including the virus titer loss due to lyophilization process (i.e. virus titer loss at day 4, 7, 28, 60 and/or 90 in the following examples).

As previously indicated, the aim of the present invention is to obtain dry product whose overall virus titer loss is limited overtime at temperature above 0° C., more preferably between 4° C. and 25° C. and more preferably at about 4° C. or 5° C. Since, it is time-consuming to wait for real time stability data (1-2 years at 2-8° C.), stability tests may typically be performed at elevated temperatures, such as 45° C. for about 3-5 days, and their results correlated to what can be expected at lower temperature, using the Arrhenius equation.

The protocol used for virus titration of formulation before freeze-drying and of reconstituted compositions has been performed on BHK-21 cells using plaque assay technique. In such a method, the number of plaque forming units (pfu/mL) is determined in a sample. A viral plaque is formed when a virus infects a cell within the fixed cell monolayer (Kaufmann and Kabelitz, 2002, Methods in Microbiology Vol. 32: Immunology of Infection. Academic Press. ISBN 0125215320). The specific steps performed for each of the following exemplified formulation according to the invention is detailed in the "EXAMPLES" part hereinafter.

Example 1: Preparation of Liquid Poxvirus-Containing Formulation to be Freeze-Dried The hereinafter referenced liquid formulation I to V have been prepared according to the following steps. These formulations comprise MVA-based products. More precisely, formulations I to III comprise TG4001 and formulations IV and V comprise TG4040.

a) TG4001 and TG4040 were initially maintained in a frozen state in Solution A1 and Solution A2, respectively. The content of each solutions Aa (comprising TG4001) and A2 (comprising TG4040) is detailed in the following Table 1.

TABLE 1

|  | Solution A1 (for preparing formulations I to III) | Solution A2 (for preparing formulations IV and V) |
| --- | --- | --- |
| Virus titer (Pfu/mL) | 2.40E+08 | 3.20E+08 |
| Saccharose (%) | 5 | 5 |
| Monosodium Glutamate | 10 mM | 10 mM |
| NaCl | 50 mM | 50 mM |
| TRIS | — | 10 mM |
| $Na_2HPO_4/KH_2PO_4$ | 10 mM | — |
| pH | 7.5 ± 0.5 | 7.5 ± 0.5 |

Solutions A1 and A2 were thawed out.

If necessary, Solutions A1 and A2 can be further diluted according to methods well-known by the person skilled in the art. For instance, solution A1 was not further diluted and was used as such in order to prepare formulations I to III. Concerning Solution A2, it has been diluted with a solution A'2 corresponding to the above-described Solution A2 (not including TG4040) in order to get a final virus titer of 6.70E+07 pfu/mL.

The obtained virus suspensions were then homogenized by stirring briefly.

b) Then, 170 μl of the following Solutions B were added to 340 μL of viral solutions A1 and A2 respectively, as obtained in step a).

More precisely:

170 μl of solutions B1 to B3 were added to 340 μL of viral solution A1 of step a) comprising TG4001, in order to prepare formulations I to III, and 170 μl of solutions B4 and B5 were added to 340 μL of viral solutions A'2 of step a) comprising TG4040, in order to prepare formulations IV and V.

The mixtures were then homogenized by stirring briefly.

The detailed compositions of Solutions B1 to B5 are given in the following Table 2.

TABLE 2

|  | Solution B1 for formulation I | Solution B2 for formulation II | Solution B3 for formulation III | Solution B4 for formulation IV | Solution B5 for formulations V |
| --- | --- | --- | --- | --- | --- |
| PVP 25 (%) | 10 | 10 | 10 | 10 | 10 |
| Sucrose (%) | 5 | 5 | 5 | 5 | 5 |
| L-Arginine | 120 mM | 120 mM | 120 mM | 600 mM | 800 mM |
| Mono sodium Glutamate | 20 mM | 20 mM | 20 mM | 20 mM | 20 mM |
| NaCl | 100 mM | 100 mM | 100 mM | 100 mM | — |
| TRIS | — | — | — | 20 mM | 20 mM |
| $Na_2HPO_4/KH_2PO_4$ | — | 20 mM | 60 mM | — | — |
| $Na_2HPO_4$ | — | — | — | 4 mM | 4 mM |
| pH | 7.5 ± 0.5 | 7.5 ± 0.5 | 7.5 ± 0.5 | 7.5 ± 0.5 | 7.5 ± 0.5 | c) The obtained liquid compositions I to V (510 µL) before lyophilization are detailed in the following Table 3.

TABLE 3

| Components | Liquid formulation I | Liquid formulation II | Liquid formulation III | Liquid formulation IV | Liquid formulation V |
|---|---|---|---|---|---|
| Viral vector (PFU/mL) | TG4001 2.55E+08 | TG4001 1.64E+08 | TG4001 1.55E+08 | TG4040 4.25E+07 | TG4040 3.75E+07 |
| PVP (25 MW) (g/L) | 33.25 | 33.25 | 33.25 | 33.25 | 33.25 |
| Saccharose (g/L) | 50 | 50 | 50 | 50 | 50 |
| Monosodium Glutamate (g/L) | 2.49 | 2.49 | 2.49 | 2.49 | 2.49 |
| L-Arginine (g/L) | 8.43 | 8.43 | 8.43 | 42.13 | 56.04 |
| NaCl (g/L) | 3.89 | 3.89 | 3.89 | 3.89 | 1.94 |
| TRIS (g/L) | — | — | — | 1.61 | 1.61 |
| $Na_2HPO_4$ (g/L) | 0.79 | 1.59 | 3.17 | 0.19 | 0.19 |
| $KH_2PO_4$ (g/L) | 0.15 | 0.29 | 0.58 | — | — |
| pH | 7.5 ± 0.5 | 7.5 ± 0.5 | 7.5 ± 0.5 | 7.5 ± 0.5 | 7.5 ± 0.5 |

The above-described liquid formulations I to V are also part of the present invention.

Example 2: Preparation of Corresponding Freeze-Dried Formulations I to V

In the following examples, all lyophilizations were done in a Lyophilizer TELSTAR LYOBETA 25.
The lyophilization protocol was the following.
a) Preparation of Dry Products I to III
TopLyo® vials (SCHOTT™) were filled with liquid formulations I to III as previously obtained in example 1 and the lyophilization process was carried out as follows:

| Freezing step | | | | |
|---|---|---|---|---|
| Description | Pression (mbar) | Temperature (° C.) | Ramp (h:min) | Stabilization (h:min) |
| Loading | AP (Atmospheric Pressure) | RT | | |
| Freezing | AP | −45 | 2:00 | 0:30 |

| Primary drying step | | | | |
|---|---|---|---|---|
| Description | Pression (mbar) | Temperature (° C.) | Ramp (h:min) | Stabilization (h:min) |
| Primary 1 | 0.1 | −10 | 0:15 | |
| Primary 2 | 0.1 | −35 | 5:00 | 8:00 |

| Secondary drying step | | | | |
|---|---|---|---|---|
| Description | Pression (mbar) | Temperature (° C.) | Ramp (h:min) | Stabilization (h:min) |
| Secondary drying 1 | 0.0047 mbar | 40 | 0:15 | 8:00 |
| Secondary drying 2 | 0.0047 mbar | 20 | 0:30 | | b) Preparation of Dry Products IV and V
TopLyo® vials (SCHOTT™) were filled with liquid formulations IV and V as previously obtained in example 1 and the lyophilization process was carried out as follows. The protocol is similar to the one carried out for formulations I to III, but a further step of vacuum is performed in this case.

| Freezing | | | | |
|---|---|---|---|---|
| Description | Pression (mbar) | Temperature (° C.) | Rampe (h:min) | Stabilisation (h:min) |
| Loading | Atm. P. | Room T | | |
| Freezing | Atm. P. | −50 | 2:00 | 0:30 |

| Primary Drying | | | | |
|---|---|---|---|---|
| Description | Pression (mbar) | Temperature (° C.) | Rampe (h:min) | Stabilisation (h:min) |
| Primary 1 | 0.150 | −35 | 0:15 | 18:00 |
| Primary 2 | 0.150 | −10 | 1:00 | 0 |

| Secondary Drying | | | | |
|---|---|---|---|---|
| Description | Pression (mbar) | Temperature (° C.) | Rampe (h:min) | Stabilisation (h:min) |
| Secondary drying 1 | minimum | 40 | 2:00 | 8:00 |
| Secondary drying 1 | minimum | 20 | 1:00 | |
| Secondary drying 2 | minimum | 10 | 0:02 | 3:00 |

The obtained dry products I to V formed a cake of suitable aspect, i.e. a smooth, white "cake" which is not retracted from the sides of the vial after lyophilization.
The respective virus titer of said products I to V after freeze-drying is detailed in the following Table 4.

TABLE 4

| Components | Dry product I | Dry product II | Dry product III | Dry product IV | Dry product V |
|---|---|---|---|---|---|
| Viral vector (PFU/mL) | TG4001 1.44E+08 | TG4001 1.21E+08 | TG4001 1.27E+08 | TG4040 2.07E+07 | TG4040 2.18E+07 |

Dry products I to V are also part of the present invention.

Said cakes were milled and the obtained powder was then reconstituted in order to determine the virus titer according to the previously described virus titration method.

Example 3: Stability Studies: Evaluation of Overall Virus Titer Losses, i.e. During Storage Overtime, Including Loss Due to Lyophilization Process 3.a) Reconstitution of Dry Products I to V
Reconstituted materials (Reconstit. Compo.) I to V prepared with WFI in a final volume of 680 µL just after lyophilization are detailed in the following Table 5 (i.e. without storage period for t0).

TABLE 5

| Components | Reconstit. Compo. I | Reconstit. Compo. II | Reconstit. Compo. III | Reconstit. Compo. IV | Reconstit. Compo. V |
|---|---|---|---|---|---|
| Viral vector (PFU/mL) | TG4001 1.44E+08 | TG4001 1.21E+08 | TG4001 1.27E+08 | TG4040 2.07E+07 | TG4040 2.18E+07 |
| PVP 25 (g/L) | 25 | 25 | 25 | 25 | 25 |
| Saccharose (g/L) | 37.5 | 37.5 | 37.5 | 37.5 | 37.5 |
| Monosodium Glutamate (g/L) | 1.9 | 1.9 | 1.9 | 1.9 | 1.9 |
| L-Arginine (g/L) | 6.3 | 6.3 | 6.3 | 31.6 | 42.1 |
| NaCl (g/L) | 2.9 | 2.9 | 2.9 | 2.9 | 1.5 |
| TRIS (g/L) | — | — | — | 1.2 | 1.2 |
| $Na_2HPO_4$ (g/L) | 0.60 | 1.19 | 2.39 | 0.14 | 0.14 |
| $KH_2PO_4$ (g/L) | 0.11 | 0.22 | 0.44 | — | — |
| pH | 7.5 ± 0.5 | 7.5 ± 0.5 | 7.5 ± 0.5 | 7.5 ± 0.5 | 7.5 ± 0.5 |

In order to evaluate the virus titer of dry products I to V after the storage at either 5° C. or 45° C. for the indicated period of time, the dry products I to V needed first to be reconstituted. In the following examples, they were reconstituted with WFI in a final volume of 680 μL and the respective viral titers were evaluated according to the previously detailed plaque assays technique.

Reconstituted materials I to V are also part of the present invention.

3.b) Evaluation of the Virus Titer Loss of Dry Compositions I to V at 5° C.

As previously indicated, the cumulated virus titer loss of each dry product (i.e. loss during storage overtime including the loss due to lyophilization process) was evaluated using the plaque assays technique on BHK-21 cells.

The steps performed in this regard for each of the compositions I to V is detailed hereinafter.

1. Cells Spreading

Host cells BHK-21 were grown in monolayers in DMEM. At confluency, the cells were washed with 10 mL PBS and then trypsinated. After removing trypsine, cells were then resuspended in 10 mL DMEM with 10% SFV at 37° C.

Then, cells suspension were homogenized and distributed in the multi-well plates (2 mL in each of the 6 wells of the plate). Then, said plates were incubated at 37° C., 5% CO2.

2. Cells Infection

About 1 day after cells spreading, aliquots of virus suspensions were added in each well comprising the BHK-21 cells of step 1. If necessary, said suspensions were firstly diluted serially in PBS, cations 100× and 1% SVF, according to method well known by the person skilled in the art. Depending on the case, the virus suspensions which were added to BHK-21 cells of step 1 were either liquid virus-containing compositions before freeze-drying or reconstituted virus-containing composition (i.e after lyophilization, at different time periods and temperatures).

Culture medium was then removed and after stirring during 60 minutes at room temperature, 2 mL of the infection medium (DMEM+5% SVF) were distributed in each well. Plates were then incubated at 37° C., 5% CO2.

3. Cells Fixation

After the medium has been removed, cells were washed with PBS (about 1 mL per well). Then, 1 mL of a solution methanol/acetone (50/50) was added and the resulting mixture was gently stirred at room temperature.

The plates were then let to be dried at room temperature.

4. Detection and Titer Determination

Virus titer determination was performed according to well-known peroxydase reaction using anti-vaccine antibodies and anti-rabbit antibodies combined with peroxydase. More precisely, before reaction anti-vaccine antibodies were diluted 100 times in PBS+2% SVF. Then, 500 μL of said antibodies were added in each well and incubated at 37° C. during about 30 minutes and then washed 3 times with 1 mL PBS+1% Triton X-100.

The reaction with anti-rabbit antibodies combined with peroxydase was carried out in the same manner, except that before reaction, said antibodies are diluted 200 times in PBS+2% SVF.

The DAB solution was prepared by dissolving one commercial DAB tablet in 15 mL of TRIS 0.05M. Then, the obtained solution was filtrated on a filtration unit NALGENE of 2 μm and the resulting filtrated solution was added to 15 μL of aqueous solution of $H_2O_2$ 30%. Once prepared, 1 mL of the DAB solution was added to each well and let until a brown coloration has appeared. The coloration solution was subsequently removed and results are visually interpreted.

Then, the infectious titer was calculated in PFU/mL, using the following formula:

$$[\text{mean of viral plaques numbers} \times 4] \times \text{dilution factor} = \text{number of PFU/mL}$$

Results

The results of the stability study at 5° C. are presented in the following Table 6, wherein:

SD=Standard Deviation.

The virus titer at day −1 corresponds to the virus titer of liquid compositions I to V before lyophilization.

The virus titer at day 0 corresponds to the virus titer of dry compositions I to V, just after lyophilization. Its comparison with the virus titer of liquid compositions I to V before lyophilization allows determining the virus titer loss during lyophilization.

The virus titer at days 28, 60 and 90 corresponds to the virus titer of dry compositions I to V after storage periods of 28, 60 and 90 days, respectively. Its comparison with the virus titer of reconstituted compositions I to V just after lyophilization (i.e. at day 0) allows determining the virus titer loss during storage at 5° C.

TABLE 6

| | (At +5° C.) | | | |
|---|---|---|---|---|
| | days | Titration mean (3 samples) PFU/mL | Log (mean) | cumulated loss | SD |
| composition I | −1 | 2.55E+08 | 8.28* | 0.00 | 0.09 |
| | 0 | 1.44E+08 | 8.16 | −0.12 | 0.07 |
| | 28 | 1.15E+08 | 8.06 | −0.22 | 0.04 |
| | 60 | 1.08E+08 | 8.03 | −0.25 | 0.05 |
| | 90 | 9.85E+07 | 7.99 | −0.29 | 0.06 |
| composition II | −1 | 1.64E+08 | 8.09* | 0.00 | 0.04 |
| | 0 | 1.21E+08 | 8.08 | −0.01 | 0.10 |
| | 28 | 1.34E+08 | 8.13 | 0.04 | 0.04 |
| | 60 | 1.16E+08 | 8.07 | −0.03 | 0.00 |
| | 90 | 9.70E+07 | 7.99 | −0.10 | 0.01 |
| composition III | −1 | 1.55E+08 | 8.07* | 0.00 | 0.06 |
| | 0 | 1.27E+08 | 8.10 | 0.04 | 0.11 |
| | 28 | 1.09E+08 | 8.04 | −0.03 | 0.15 |

TABLE 6-continued (At +5° C.)

| | days | Titration mean (3 samples) PFU/mL | Log (mean) | cumulated loss | SD |
|---|---|---|---|---|---|
| | 60 | 1.09E+08 | 8.04 | −0.03 | 0.07 |
| | 90 | 9.60E+07 | 7.98 | −0.08 | 0.02 |
| composition IV | −1 | 4.25E+07 | 7.50* | 0.00 | 0.07 |
| | 0 | 2.07E+07 | 7.32 | −0.19 | 0.06 |
| | 28 | 1.71E+07 | 7.23 | −0.27 | 0.05 |
| | 60 | 1.58E+07 | 7.20 | −0.31 | 0.01 |
| | 90 | 2.40E+07 | 7.38 | −0.12 | 0.08 |
| composition V | −1 | 3.75E+07 | 7.45* | 0.00 | 0.09 |
| | 0 | 2.18E+07 | 7.34 | −0.11 | 0.06 |
| | 28 | 1.50E+07 | 7.18 | −0.27 | 0.03 |
| | 60 | 1.58E+07 | 7.20 | −0.25 | 0.05 |
| | 90 | 2.39E+07 | 7.38 | −0.07 | 0.16 |

*means that the log means has been adapted to a 680 μL volume (=log(titration mean × 0.510/0.680))

As expected, dry products I to V are stable at 5° C. Actually, their cumulated virus titer losses is no more than 0.6 log after at least 90 days of storage at 5° C.

3.c) Evaluation of the Virus Titer Loss of Dry Products I to V at 45° C.

In order to further assess the stability of dry products I to V, stability studies have been performed at 45° C. As previously explained, such an elevated temperature allows predicting the degradation of the virus in an accelerated manner.

Each dry product I to V was stored for 4, 28, 60 and 90 days at 45° C.

The cumulated virus titer loss of each dry product (i.e. loss during storage overtime including the loss due to lyophilization process) was evaluated using titration method (plaque assays technique on BHK-21 cells) as previously described.

Results

The results of the accelerated stability study at 45° C. are presented in the following Table 7, wherein:

SD, the virus titer at day-1 and the virus titer at day 0 have the same meaning than in the previous Table 6.

The virus titer at days 4, 7, 28 and 60 corresponds to the virus titer of dry compositions I to V after storage periods of 4, 7, 28 and 60 days, respectively. Its comparison with the virus titer of reconstituted compositions I to V just after lyophilization (i.e. at day 0) allows determining the virus titer loss during storage at 45° C.

TABLE 7

(At +45° C.)

| | days | Titration mean (3 samples) PFU/mL | Log (mean) | Cumulated loss | SD |
|---|---|---|---|---|---|
| composition I | −1 | 2.55E+08 | 8.28* | 0.00 | 0.09 |
| | 0 | 1.44E+08 | 8.16 | −0.12 | 0.07 |
| | 4 | 7.60E+07 | 7.88 | −0.40 | 0.09 |
| | 28 | 5.87E+06 | 6.77 | −1.51 | 0.08 |
| | 60 | 7.55E+05 | 5.88 | −2.40 | 0.03 |
| composition II | −1 | 1.64E+08 | 8.09* | 0.00 | 0.04 |
| | 0 | 1.21E+08 | 8.08 | −0.01 | 0.10 |
| | 4 | 5.88E+07 | 7.77 | −0.32 | 0.10 |
| | 28 | 8.63E+06 | 6.94 | −1.15 | 0.03 |
| | 60 | 6.00E+05 | 5.78 | −2.31 | 0.11 |
| Composition III | −1 | 1.55E+08 | 8.07* | 0.00 | 0.06 |
| | 0 | 1.27E+08 | 8.10 | 0.04 | 0.11 |
| | 4 | 6.53E+07 | 7.82 | −0.25 | 0.12 |

TABLE 7-continued (At +45° C.)

| | days | Titration mean (3 samples) PFU/mL | Log (mean) | Cumulated loss | SD |
|---|---|---|---|---|---|
| | 28 | 7.53E+06 | 6.88 | −1.19 | 0.14 |
| | 60 | 1.22E+06 | 6.09 | −1.98 | 0.07 |
| composition IV | −1 | 4.25E+07 | 7.50* | 0.00 | 0.07 |
| | 0 | 2.07E+07 | 7.32 | −0.19 | 0.06 |
| | 3 | 8.68E+06 | 6.94 | −0.57 | NA |
| | 3.5 | 8.14E+06 | 6.91 | −0.59 | NA |
| | 4 | 7.67E+06 | 6.88 | −0.62 | NA |
| | 7 | 5.80E+06 | 6.76 | −0.74 | 0.07 |
| | 28 | 1.67E+06 | 6.22 | −1.28 | 0.04 |
| | 60 | 6.85E+05 | 5.84 | −1.67 | 0.05 |
| composition V | −1 | 3.75E+07 | 7.45* | 0.00 | 0.09 |
| | 0 | 2.18E+07 | 7.34 | −0.11 | 0.06 |
| | 3 | 6.97E+06 | 6.84 | −0.61 | NA |
| | 3.5 | 6.46E+06 | 6.81 | −0.64 | NA |
| | 4 | 6.03E+06 | 6.78 | −0.67 | NA |
| | 7 | 4.33E+06 | 6.64 | −0.81 | 0.08 |
| | 28 | 1.23E+06 | 6.09 | −1.36 | 0.17 |
| | 60 | 4.33E+05 | 5.64 | −1.81 | 0.16 |

*means that the log means has been adapted to a 680 μL volume (log(titration mean × 0.510/0.680))
NA = Not applicable It is to be noted that in the above Table 7, the results indicated for compositions IV and V at days 3, 3.5 and 4 at 45° C. have been estimated according to statistical analysis as described below, i.e. using the software SAS 9.2 and order 1 Arrhenius principle-based multivariate model which is defined with the following equation:

$$\ln\left(\ln\left(\frac{C_0}{C}\right)\right) = \beta_0 + \beta_1 * \frac{1}{T} + \beta_2 * \ln(t)$$

where:
$C_0$ is the initial titer in pfu/mL (after lyophilisation),
T is the temperature in Kelvin degrees,
t is the time in days,
C is the titer at the corresponding time t in pfu/mL.

Since only one temperature is used in the present example, i.e. 45° C., the equation can be simplified:

$$\ln\left(\ln\left(\frac{C_0}{C}\right)\right) = \beta_0 + \beta_2 * \ln(t)$$

When the parameters of the model are estimated, the titer at a given time point can be estimated by the following formula:

$$\hat{C} = \frac{C_0}{\exp\left(\exp\left(\hat{\beta}_0 + \hat{\beta}_2 * \ln(t)\right)\right)}$$

Where:
$C_0$ is the initial titer in pfu/mL (after lyophilisation),
t is the time in days,
$\hat{C}$ is the estimated titer at the corresponding time t in pfu/mL,
$\hat{\beta}_0, \hat{\beta}_2$ are the estimated parameters of the model.
And the loss estimation is then estimated by:

$$\hat{L} = \log(\hat{C}) - \log(C_{-1} * 0.51/0.68)$$

where:
- $\hat{C}$ is the estimated titer in pfu/mL,
- $C_{-1}$ is the titer one day before the lyophilisation in pfu/mL,
- $\hat{L}$ is the estimated loss.

Concerning composition IV, the adjusted $R^2$, equal to 0.995, means that the model fit correctly to the data.

Concerning composition IV, the adjusted $R^2$, equal to 0.999, means that the model fit correctly to the data.

Thus, the above-described results show that liquid formulations I to V allow preserving the virus stability following heat challenge that occurs during lyophilization process and that further virus stability was further preserved during long-term stability tests.

To conclude, in formulations according to the present invention, viruses were protected against damage caused by thermal stresses, both during lyophilisation process (i.e. due to freezing, freeze-drying and thawing out steps) and during storage at temperatures above 0° C., more particularly at about 5° C.

Example 4: Formulation of Viral Preparation without Phosphate

Three reference samples (RS2 to RS4) were generated from a purified batch of TG4040 and one (RS1) from a purified TG4001 viral batch. The references samples were treated together with the compositions I to V described in examples 1 to 3 except that the RS samples were formulated without phosphate. The concentrations of Arg and NaCl were also varying according to the sample.

As described above, 340 µL of viral solution was mixed to 170 µL of stabilizing solution. The detailed compositions of stabilizing solution for each reference product S1 to S4 are given in the following Table 8.

TABLE 8

|  | Stabilizing solution for Reference sample RS1 | Stabilizing solution for Reference sample RS2 | Stabilizing solution for Reference sample RS3 | Stabilizing solution for Reference sample RS4 |
| --- | --- | --- | --- | --- |
| PVP 25 kDa (%) | 10% | 10% | 10% | 10% |
| Sucrose (%) | 5% | 5% | 5% | 5% |
| Mono sodium Glutamate (g/L) | 20 mM | 20 mM | 20 mM | 20 mM |
| L-Arginine (g/L) | 120 mM | 120 mM | 600 mM | 800 mM |
| NaCl (g/L) | 100 mM | 100 mM | 100 mM | — |
| Tris (g/L) | 20 mM | 20 mM | 20 mM | 20 mM |
| Na$_2$HPO$_4$/KH$_2$PO$_4$ (g/L) | — | — | — | — |
| Na$_2$HPO$_4$ (g/L) | — | — | — | — |
| pH | 7.5 +/− 0.5 | 7.5 +/− 0.5 | 7.5 +/− 0.5 | 7.5 +/− 0.5 |

The obtained liquid reference products RS1 to RS4 before lyophilization are detailed in the following Table 9.

TABLE 9

|  | Reference sample RS1 | Reference sample RS2 | Reference sample RS3 | Reference sample RS4 |
| --- | --- | --- | --- | --- |
| Viral Vector (PFU/mL) | TG4001 2.95E+08 | TG4040 3.28E+07 | TG4040 3.83E+07 | TG4040 3.97E+07 |
| PVP 25 kDa (g/L) | 33.25 | 33.25 | 33.25 | 33.25 |
| Sucrose (g/L) | 50 | 50 | 50 | 50 |
| Mono sodium Glutamate (g/L) | 2.49 | 2.49 | 2.49 | 2.49 |
| L-Arginine (g/L) | 8.43 | 8.43 | 42.13 | 56.04 |
| NaCl (g/L) | 3.89 | 3.89 | 3.89 | 1.94 |
| Tris (g/L) | 1.61 | 1.61 | 1.61 | 1.61 |
| Na$_2$HPO$_4$/KH$_2$PO$_4$ (g/L) | — | — | — | — |
| Na$_2$HPO$_4$ (g/L) | — | — | — | — |
| pH | 7.5 +/− 0.5 | 7.5 +/− 0.5 | 7.5 +/− 0.5 | 7.5 +/− 0.5 |

The referenced products RS1-RS4 are then lyophilized as described above and reconstituted with WFI in a final volume of 680 µL.

The detailed compositions of the reconstituted reference products RS1 to RS4 (680 µL) prepared just after lyophilization process (i.e. without storage period) are detailed in the following Table 10.

TABLE 10

|  | Reference sample RS1 | Reference sample RS2 | Reference sample RS3 | Reference sample RS4 |
| --- | --- | --- | --- | --- |
| Viral Vector (PFU/mL at $t_0$ after lyophilization) | TG4001 1.66E+08 | TG4040 2.20E+07 | TG4040 1.96E+07 | TG4040 2.45E+07 |
| PVP 25 KDa (g/L) | 25 | 25 | 25 | 25 |
| Sucrose (g/L) | 37.5 | 37.5 | 37.5 | 37.5 |
| Mono sodium Glutamate (g/L) | 1.9 | 1.9 | 1.9 | 1.9 |
| L-Arginine (g/L) | 6.3 | 6.3 | 61.6 | 42.1 |
| NaCl (g/L) | 2.9 | 2.9 | 2.9 | 1.5 |
| Tris (g/L) | 1.2 | 1.2 | 1.2 | 1.2 |
| Na$_2$HPO$_4$/KH$_2$P0$_4$ (g/L) | — | — | — | — |
| Na$_2$HPO$_4$ (g/L) | — | — | — | — |
| pH | 7.5 +/− 0.5 | 7.5 +/− 0.5 | 7.5 +/− 0.5 | 7.5 +/− 0.5 |

Stability studies were performed at 5° C. and 45° C. as described in Example 3. For this purpose, each dry reference product RS1 to RS4 was stored at 5° C. or 45° C. for a period of time and the cumulated virus titer loss (i.e. loss during storage overtime including the loss due to lyophilization process) was evaluated at various time point using the titration method previously described.

The results of the stability of TG4001 and TG4040 formulations at 5° C. are given in the following Table 11.

TABLE 11

| +5° C. | days | Titration mean (3 samples) PFU/mL | Log (mean) | Cumulated loss | SD des log |
| --- | --- | --- | --- | --- | --- |
| Reference sample RS1 TG4001 | −1 | 2.95E+08 | 8.34 | 0.00 | 0.05 |
|  | 0 | 1.66E+08 | 8.22 | −0.12 | 0.10 |
|  | 28 | 1.97E+08 | 8.29 | −0.05 | 0.10 |
|  | 60 | 1.24E+08 | 8.09 | −0.25 | 0.06 |
|  | 90 | 1.18E+08 | 8.07 | −0.27 | 0.03 |

TABLE 11-continued

| +5° C. | days | Titration mean (3 samples) PFU/mL | Log (mean) | Cumulated loss | SD des log |
|---|---|---|---|---|---|
| Reference sample RS2 | −1 | 3.28E+07 | 7.39 | 0.00 | 0.04 |
| | 0 | 2.20E+07 | 7.34 | −0.05 | 0.12 |
| | 28 | 1.43E+07 | 7.16 | −0.24 | 0.06 |
| | 60 | 1.64E+07 | 7.22 | −0.18 | 0.04 |
| | 90 | 1.60E+07 | 7.20 | −0.19 | 0.06 |
| Reference sample RS3 | −1 | 3.83E+07 | 7.46 | 0.00 | 0.03 |
| | 0 | 1.96E+07 | 7.29 | −0.17 | 0.07 |
| | 28 | 1.72E+07 | 7.24 | −0.22 | 0.03 |
| | 60 | 1.85E+07 | 7.27 | −0.19 | 0.02 |
| | 90 | 2.24E+07 | 7.35 | −0.11 | 0.21 |
| Reference sample RS4 | −1 | 3.97E+07 | 7.47 | 0.00 | 0.07 |
| | 0 | 2.45E+07 | 7.39 | −0.08 | 0.11 |
| | 28 | 1.85E+07 | 7.27 | −0.21 | 0.07 |
| | 60 | 1.64E+07 | 7.22 | −0.26 | 0.02 |
| | 90 | 1.99E+07 | 7.30 | −0.17 | 0.12 |

The results of the stability of TG4001 and TG4040 formulations at 45° C. are given in the following Table 12.

TABLE 12

| +45° C. | days | Titration mean (3 samples) PFU/mL | Log (mean) | Cumulated loss | SD |
|---|---|---|---|---|---|
| Reference sample TG4001 (RS1) | −1 | 2.95E+08 | 8.34 | 0.00 | 0.05 |
| | 0 | 1.66E+08 | 8.22 | −0.12 | 0.10 |
| | 4 | 5.87E+07 | 7.77 | −0.58 | 0.08 |
| | 28 | 3.96E+06 | 6.60 | −1.75 | 0.19 |
| | 60 | 1.28E+05 | 5.11 | −3.24 | 0.05 |
| Reference sample TG4040 (RS2) | −1 | 3.28E+07 | 7.39 | 0.00 | 0.04 |
| | 0 | 2.20E+07 | 7.34 | −0.05 | 0.12 |
| | 4 | 5.35E+06 | 6.73 | 0.66 | NA |
| | 28 | 1.17E+05 | 5.07 | −2.32 | 0.04 |
| | 60 | 1.54E+03 | 3.19 | −4.20 | 0.12 |
| Reference sample (RS3) | −1 | 3.83E+07 | 7.46 | 0.00 | 0.03 |
| | 0 | 1.96E+07 | 7.29 | −0.17 | 0.07 |
| | 4 | 5.62E+06 | 6.75 | −0.71 | NA |
| | 28 | 1.76E+06 | 6.25 | −1.21 | 0.02 |
| | 60 | 7.40E+05 | 5.87 | −1.59 | 0.12 |
| Reference sample RS4 | −1 | 3.97E+07 | 7.47 | 0.00 | 0.07 |
| | 0 | 2.45E+07 | 7.39 | −0.08 | 0.11 |
| | 4 | 6.74E+06 | 6.83 | −0.64 | NA |
| | 28 | 6.33E+05 | 5.80 | −1.67 | 0.12 |
| | 60 | 2.48E+05 | 5.40 | −2.08 | 0.23 |

Figure 1B:
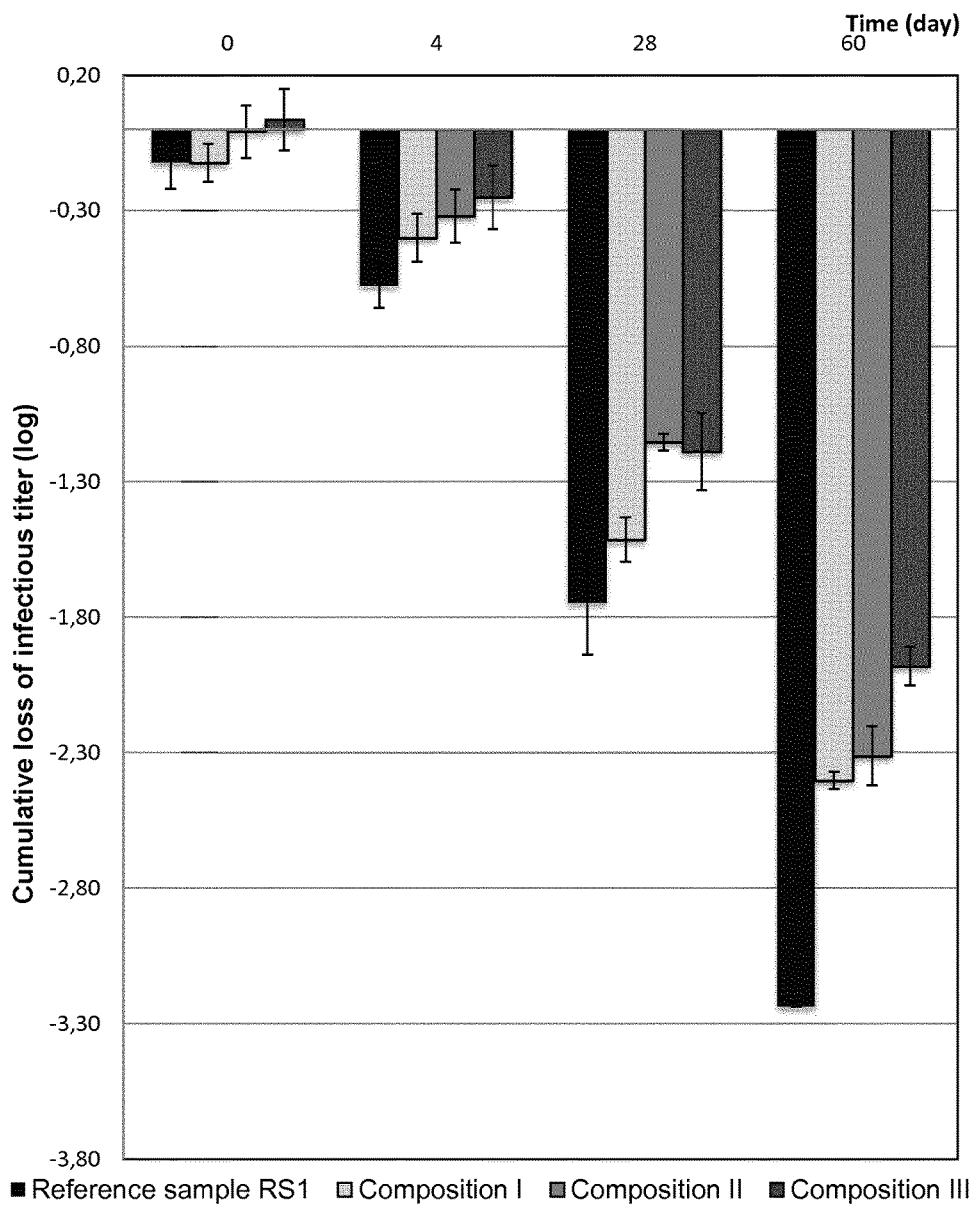
(FIG. 1B) for the indicated period of time. Light grey bars represent composition I, middle grey bars represent composition II, dark grey bars represent composition III and black bars represent reference sample RS1 described hereinafter.

As illustrated in FIG. 1 and Tables 6 and 11, the presence of phosphate is beneficial to the stability of viral preparations. Indeed, the cumulative loss of infectious TG4001 titer after 28, 60 or 90 days at 5° C. is reduced in the presence of phosphate buffer as compared to in its absence (see FIG. 1A). For example, after 60 days at 5° C., cumulative loss is of −0.25 for composition I comprising 0.94 g/L of phosphate buffer, −0.03 log for compositions II and III comprising 1.88 g/L and 3.75 g/L of phosphate buffer as compared to −0.25 log for reference sample RS1 formulated in the absence of phosphate. The increased stability provided by phosphate buffer-comprising formulations was also observed in the accelerated stability studies; resulting in cumulative titer losses of about −2 log after 60 days at 45° C. in the presence of phosphate (−2.40 log, −2.31 log and −1.98 log for compositions I, II and III, respectively) versus more than −3 log in the absence of phosphate (−3.24 log for RS1).

The same tendency is observed with TG4040 formulations. For example cumulative loss measured after 90 days at +5° C. for RS4 sample is more important than the one detected with formulation V (−0.17 log and −0.07 log respectively). This effect is also observed after 60 days at 45° C. (−2.08 log versus −1.81 log respectively).

Example 5: Long Term Stability

TG4040 viral preparations were formulated as described above. More particularly, two different concentrations were tested; respectively a high dose (about $1.70 \times 10^8$ pfu/mL) and a low dose (about $7.00 \times 10^7$ pfu) and the viral preparations were formulated in formulations containing 1 mM $Na_2HPO_4$ and Tris 10 mM; Glutamate Na 10 mM, sucrose 3.75%, NaCl 50 mM, PVP 25 kDa 2.5% and 30 mM Arg). A formulation with 150 mM of Arg was also tested with the low dose TG4040 preparation.

The three TG4040 formulations were treated as described above and lyophilized according to a semi industrial process (IDT). The dried-freeze product was reconstituted and virus stability was assessed at 5° C. for a period of time of one year (virus loss was assessed before lyophilization, just after reconstitution (to) and at 28, 90, 180, 270 and 365 days at 5° C.

A total virus loss inferior to −0.60 log after one year at 5° C. was observed for each TG4040 formulation (respectively −0.33 log for the high dose formulation in 30 mM Arg; −0.42 log for the low dose formulation in 30 mM Arg and −0.24 log for the low dose formulation in 150 mM Arg).

All together, these results highlight that the presence of phosphate is beneficial to the stability of viral preparation. Arg plays also a role in virus stability especially when the virus concentration before lyophilization is lower than $10^8$ PFU/mL. The product matrix containing residual proteins is diluted at low virus concentration in the same manner; these proteins could contribute to stabilize the virus at high concentration. Arg will replace the stabilization role of residual protein in the matrix during the freeze drying operation.

All documents (e.g. patents, patent applications, publications) cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A freeze-dried formulation comprising (i) at least one attenuated or recombinant poxvirus-based material, (ii) between 5 g/L and 80 g/L of at least one polymer selected from the group consisting of polyvinylpyrrolidone and derivatives thereof, (iii) between 20 g/L and 80 g/L of at least one disaccharide, (iv) arginine and glutamate, (v) between 0.1 g/L and 5 g/L of at least one pharmaceutical acceptable phosphate salt, and between 1 g/L and 5 g/L of at least one pharmaceutical acceptable monovalent salt and, optionally (vi) a pharmaceutical acceptable buffer wherein the pH of the formulation is comprised between about 7 and about 8.5.

2. The formulation of claim 1, wherein said (ii) at least one polymer is selected from the group consisting of polyvinylpyrrolidone and derivatives thereof, and mixture thereof.

3. The formulation of claim 2, wherein said polyvinylpyrrolidone or derivatives thereof have a molecular weight comprised between 10 kDa and 40 kDa.

4. The formulation of claim 2, wherein said formulation comprises between 10 g/L and 50 g/L of polyvinylpyrrolidone or derivatives or mixture thereof.

5. The formulation of claim 1, wherein said formulation comprises at least one disaccharide selected from the group consisting of sucrose, lactulose, lactose, maltose, trehalose, cellobiose, isomaltose and maltulose.

6. The formulation of claim 1, wherein said formulation comprises 50 g/L of disaccharide, and wherein said disaccharide is sucrose.

7. The formulation of claim 1, wherein said formulation comprises between 5 g/L and 100 g/L of arginine.

8. The formulation of claim 1, wherein said formulation comprises between 1 g/L and 10 g/L of glutamate.

9. The formulation of claim 1, wherein at least one of said phosphate salt is selected from the group consisting of sodium and potassium salts, and combination thereof.

10. The formulation of claim 9, wherein said phosphate salt is selected from the group consisting of monobasic phosphate salts, dibasic phosphate salts and tribasic phosphate salts.

11. The formulation of claim 1, wherein said at least one pharmaceutically acceptable monovalent salt is selected from the group consisting of sodium chloride and potassium chloride.

12. The formulation of claim 1, wherein said poxvirus-based material is a virus or viral particle selected from the group consisting of Vaccinia Virus (VV) and modified Vaccinia Virus Ankara (MVA).

13. The formulation of claim 12, wherein said poxvirus-based material is a recombinant MVA selected from the group consisting of a MVA expressing HCV NS3, NS4 and NS5B antigens; a MVA expressing the MUC-1 antigen and IL-2; and a MVA expressing non oncogenic E6 and E7 antigens of HPV-16 and IL-2.

14. The formulation of claim 12, wherein said poxvirus-based material is a recombinant Vaccinia Virus selected from the group consisting of a thymidine kinase (TK)-inactivated vaccinia virus expressing an immune-stimulating cytokine which is a granulocyte macrophage colony stimulating factor and a doubly thymidine kinase (TK-) and ribonucleotide reductase (I4L-) inactivated vaccinia virus expressing a suicide gene.

15. The formulation of claim 1, wherein the titer of the poxvirus-based material in said formulation comprises between $1\times10^6$ PFU/mL and $1\times10^{10}$ PFU/mL.

* * * * *